(12) United States Patent
Tucker et al.

(10) Patent No.: US 8,192,473 B2
(45) Date of Patent: Jun. 5, 2012

(54) PHOTOTHERAPY APPARATUS FOR HAIR, SCALP AND SKIN TREATMENT

(75) Inventors: Gavin Tucker, Irvine, CA (US);
Nicholas Brox, Laguna Beach, CA (US);
Jeffrey Braile, Boca Raton, FL (US);
Morgan Pepitone, Newport Beach, CA (US)

(73) Assignee: APIRA Science, Inc., Newport Beach, CA (US)

( * ) Notice: Subject to any disclaimer, the term of this patent is extended or adjusted under 35 U.S.C. 154(b) by 0 days.

(21) Appl. No.: 12/807,911

(22) Filed: Sep. 16, 2010

(65) Prior Publication Data

US 2011/0015707 A1    Jan. 20, 2011

Related U.S. Application Data

(63) Continuation-in-part of application No. 12/586,290, filed on Sep. 18, 2009.

(60) Provisional application No. 61/136,630, filed on Sep. 19, 2008, provisional application No. 61/211,630, filed on Apr. 1, 2009.

(51) Int. Cl.
*A61N 5/06* (2006.01)
(52) U.S. Cl. .................... 607/91; 606/9; 607/90
(58) Field of Classification Search ............. 607/88–94
See application file for complete search history.

(56) References Cited

U.S. PATENT DOCUMENTS

| | | | |
|---|---|---|---|
| 4,930,504 A | 6/1990 | Diamantopoulos et al. | |
| 5,259,380 A | 11/1993 | Mendes et al. | |
| 5,549,660 A | 8/1996 | Mendes et al. | |
| 5,817,089 A | 10/1998 | Tankovich et al. | |
| 6,183,500 B1 | 2/2001 | Kohler | |
| 6,358,272 B1 * | 3/2002 | Wilden | 607/89 |
| 6,450,941 B1 | 9/2002 | Larsen | |
| 6,497,719 B2 | 12/2002 | Pearl et al. | |
| 6,666,878 B2 | 12/2003 | Carlgren | |
| 6,835,202 B2 | 12/2004 | Harth et al. | |
| 7,108,712 B2 * | 9/2006 | Barghelame | 607/91 |
| 7,194,316 B2 | 3/2007 | Bousfield et al. | |
| 7,201,764 B2 | 4/2007 | Pearl et al. | |
| D585,994 S | 2/2009 | Mulhauser et al. | |
| 7,722,656 B1 | 5/2010 | Segal | |

(Continued)

FOREIGN PATENT DOCUMENTS

GB    2 262 043 A    6/1993

(Continued)

*Primary Examiner* — Henry M Johnson, III
(74) *Attorney, Agent, or Firm* — Robert M. Downey, P.A.

(57) ABSTRACT

A wearable hands-free apparatus for providing phototherapy treatment to a number of hair, scalp and skin related conditions includes a head unit (e.g., a headset, headphones, headband, or helmet unit) with earphones to allow the user to listen to an audio program during a treatment. The head unit supports a light emitting canopy band that is fitted with an array of light generating sources, such as light emitting diodes (LEDs), laser diodes, or infrared lights, that emit light within a particular wavelength range correlating with the treatment of one or more specific hair, scalp and/or skin-related conditions. The light emitting canopy band is specifically designed to conform to the shape of the human scalp for providing complete, uniform and consistent light coverage to the areas of the scalp that are most commonly affected by hair loss in men and women. A handheld control device allows the user to select the desired treatment program and is adapted for connection to a digital audio player device, such as an MP3 player, for delivering audio signals to the earphones.

21 Claims, 17 Drawing Sheets

U.S. PATENT DOCUMENTS

| | | | |
|---|---|---|---|
| 2001/0056293 A1* | 12/2001 | Brainard | 607/88 |
| 2004/0138727 A1 | 7/2004 | Taboada et al. | |
| 2004/0153131 A1 | 8/2004 | Yorke | |
| 2005/0159796 A1* | 7/2005 | Ronn | 607/88 |
| 2006/0030908 A1 | 2/2006 | Powell et al. | |
| 2006/0161226 A1 | 7/2006 | McMickle | |
| 2006/0247742 A1 | 11/2006 | Lee | |
| 2007/0179570 A1* | 8/2007 | De Taboada et al. | 607/88 |
| 2007/0179571 A1* | 8/2007 | De Taboada et al. | 607/88 |
| 2007/0184003 A1 | 8/2007 | Gaunitz | |
| 2007/0276455 A1* | 11/2007 | Fiset | 607/91 |
| 2008/0045840 A1* | 2/2008 | Chance | 600/476 |
| 2008/0077199 A1* | 3/2008 | Shefi et al. | 607/88 |
| 2008/0103561 A1* | 5/2008 | Moscovici | 607/88 |
| 2008/0125836 A1* | 5/2008 | Streeter et al. | 607/89 |
| 2008/0221211 A1* | 9/2008 | Streeter | 514/557 |
| 2009/0012586 A1 | 1/2009 | Kepecs | |
| 2009/0024116 A1 | 1/2009 | Mulhauser et al. | |
| 2009/0032049 A1 | 2/2009 | Rabin et al. | |
| 2010/0094384 A1 | 4/2010 | Taboada | |
| 2010/0106077 A1 | 4/2010 | Rabin | |
| 2011/0015707 A1* | 1/2011 | Tucker et al. | 607/90 |
| 2011/0022132 A1 | 1/2011 | Kim | |
| 2011/0092863 A1 | 4/2011 | Kim | |

FOREIGN PATENT DOCUMENTS

| | | |
|---|---|---|
| JP | 10295767 A | 11/1998 |
| JP | 4257294 | 4/2009 |
| WO | WO 95/19808 | 7/1995 |
| WO | WO/02/098509 | 12/2002 |
| WO | WO02/102228 | 12/2002 |
| WO | WO/2004/026400 | 4/2004 |
| WO | WO 2004-026400 | 4/2004 |
| WO | WO/2004/045717 | 6/2004 |
| WO | WO/2005/009483 | 2/2005 |
| WO | WO/2005/025672 | 3/2005 |
| WO | WO/2005/065251 | 7/2005 |
| WO | WO/2005/086846 | 9/2005 |
| WO | WO/2005/110527 | 11/2005 |
| WO | WO2006/125367 A1 | 7/2006 |
| WO | WO/2006/086470 | 8/2006 |
| WO | WO2006/078613 A3 | 5/2007 |
| WO | WO/2008/144157 | 11/2008 |
| WO | WO 2008-144157 A1 | 11/2008 |
| WO | WO/2009/008967 | 1/2009 |
| WO | WO/2009/016963 | 2/2009 |
| WO | WO/2009/114840 | 9/2009 |
| WO | WO2009/131420 A3 | 10/2009 |
| WO | WO/2009/151286 | 12/2009 |

* cited by examiner

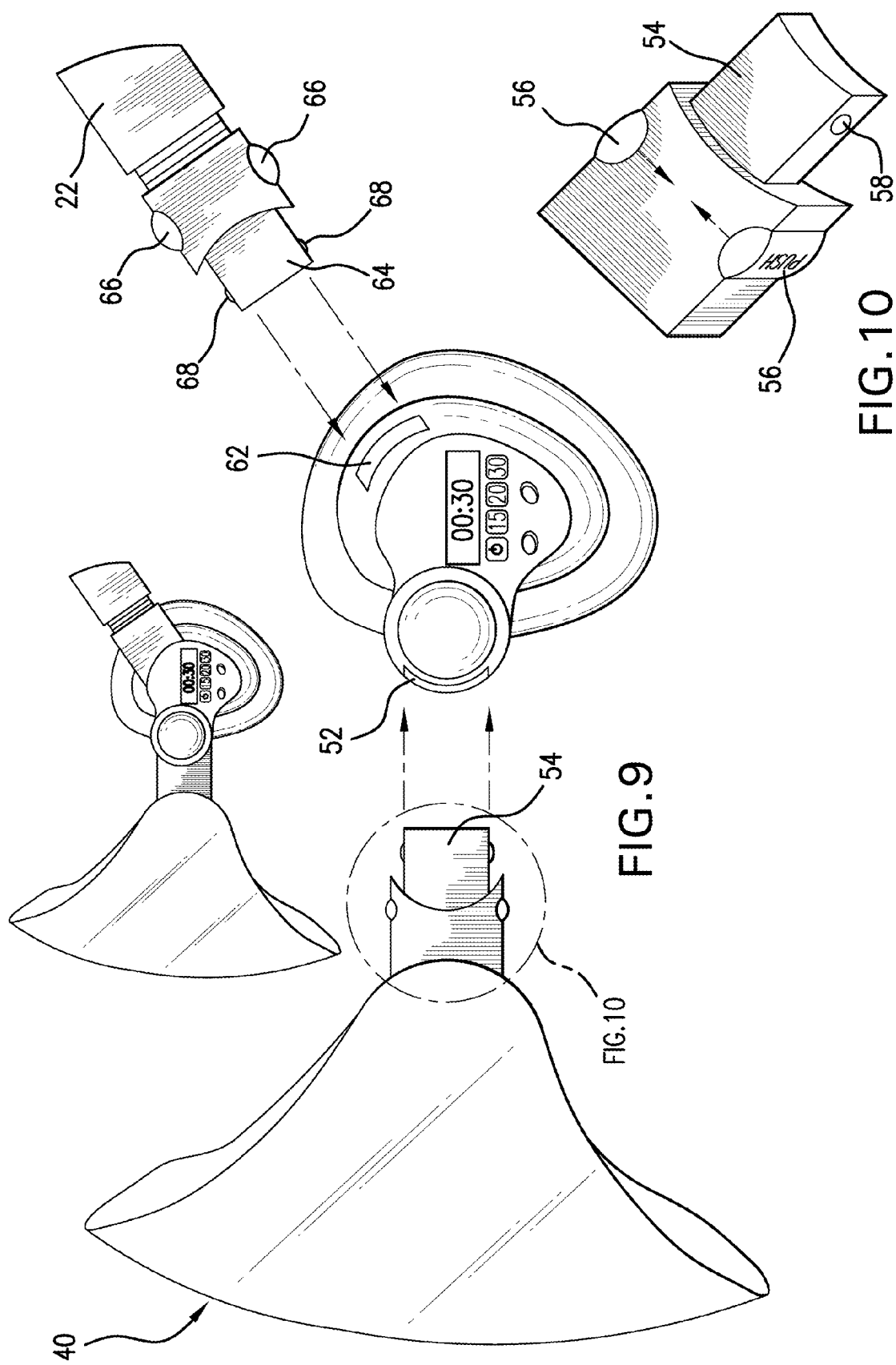

PHOTOTHERAPY APPARATUS FOR HAIR, SCALP AND SKIN TREATMENT

This application is a Continuation-In-Part (CIP) of non-provisional patent application Ser. No. 12/586,290 filed Sep. 18, 2009, which is based on two U.S. provisional patent applications: Ser. No. 61/136,630 filed on Sep. 19, 2008; and Ser. No. 61/211,630 filed on Apr. 1, 2009.

BACKGROUND OF THE INVENTION

1. Field of the Invention

This invention relates to light therapy for the treatment of skin, scalp and hair and, more particularly, to a phototherapy apparatus that includes a head canopy band having light generating sources and audio headphones along with a hand held control unit, and wherein the device is capable of providing hands-free therapeutic aid to a user's skin, scalp and/or hair by way of evenly distributed light of various beneficial wavelength that is directed onto entire treatment areas of a user's skin or scalp.

2. Discussion of the Related Art

People are frequently confronted with hair loss as well as a variety of different scalp and skin-related conditions, such as acne, sun spots, and wrinkling of the skin, psoriasis and non-melanoma skin cancer. In response, an assortment of treatment products, each typically targeting one specific hair, scalp or skin-related condition, have been developed over the past 75 years and made available to the public. Many of these products are in the form of a topical solution that requires an arduous application process. Where the condition is hair loss, a surgical process has been made available, wherein hair plugs are surgically transplanted in place of the missing hair. However, this surgical process for treating hair loss is extremely expensive and consequently, is not available to an average consumer.

More recently, the use of phototherapy to treat hair loss, as well as various skin and scalp disorders, has become increasingly popular. Phototherapy consists of exposure to specific wavelengths of light using lasers, light emitting diodes (LED's) (both individual and arrays), IPL's (Intense Pulsed Light) and other light sources, for a prescribed amount of time to both treat disease and affect cosmetic enhancements to the hair, scalp and skin. The use of phototherapy in medical science and aesthetics is rapidly evolving as more and more wavelengths of light are being identified to target various sections of cells in order to stimulate cellular proficiency and enhance the body's ability to heal and rejuvenate itself. Phototherapy is currently used to treat acne, wrinkles, sun and age spots, rosacia, eczema, hair loss and wound healing through wavelengths indicated by various colors (i.e., wavelengths) of the light spectrum. By utilizing various wavelengths, colors relatively close on the spectrum can cause different effects when applied to various parts on the body.

For example, red light at a wavelength of 670 nanometers has been clinically shown to prevent hair loss and re-grow new hair, as well as to cause increased melanin production and protein synthesis. Red and infrared lights have also been used to increase the production of collagen and to reduce redness, dilated capillaries and damage to the skin, as well as reduction of wrinkles and fine lines. Blue light has been clinically shown to reduce acne and, when combined with red light, eliminates acne and reduces the scarring often associated with acne treatment. Yellow and Amber lights have been clinically shown to reduce fine lines and wrinkles, rosacia, and can help to repair sun damaged skin. Green light has been shown to reduce and eliminate sun and age spots, lighten freckles and also help promote more luminous skin condition and overall radiance of the skin. As set forth above, many of these light sources have multiple benefits, cross over each other in treating certain ailments and work to promote a variety of benefits to the hair and skin. These light sources are often used in combinations to provide increase efficacy and various degrees of stimulation.

Science throughout the years has determined the effects of various wavelengths of light, but absorption is the key to cellular change. Light therapy emits photons which are absorbed by the skins photoreceptors. Hair and skin cells respond well to phototherapy involving low level light due to the fact that cells reside just underneath the skin surface, making these low levels of energy able to reach the receptor sites and induce photochemistry.

There are a number of phototherapy devices currently available for home use to treat both skin and hair. The majority of these are hand held devices, varying in both size and number of light sources (i.e., laser diodes, LED's, or infrared diodes). These devices are manually moved around the hair or face by the user and require a constant movement in order to expose the entire surface area to the light sources. This results in an uneven treatment protocol, as the average user is unlikely to be able to cover the entire surface area through manual movements and will leave certain areas untreated. Further, due to the need for a manageable size (must fit in the hand), these devices are often underpowered.

Several phototherapy devices have been developed that are adapted to be portably worn by a user in a hands-free mode of operation. For example, U.S. Pat. App. Pub. No. 2009/0012586 A1 to Kepecs discloses a system that houses LEDs within a head unit that resembles a baseball helmet. The Kepecs device is used for reducing hair loss, as well as the therapeutic healing of a variety of skin disorders. One particular shortcoming of the Kepecs device is the onerous task of snapping or screwing in different LEDs to alter the desired wavelength.

U.S. Pat. App. Pub. No. 2006/0030908 to Powell et al. discloses a skin treatment phototherapy device that may comprise a clamshell structure, pen shape, facial mask, or desk lamp design, and which includes multi-colored LEDs. The Powell device attempts to treat a variety of skin conditions on the face and other skin regions below the user's head. Depending on the skin condition to be treated, the corresponding wavelengths, intensity levels, and time interval for the skin treatment can be varied by a control system. However, this device is neither designed nor intended to treat hair loss. Moreover, this device lacks a suitable structure and design for directing an evenly distributed light pattern upon a user's entire scalp area.

A further example of a phototherapy device that is adapted to be worn on a user's head is disclosed in PCT International Patent Application No. JP2002/009778 to Shimizu. Shimizu discloses a phototherapy device for home use that has a head band fitted with multiple LED's. The head band is structured to span over the top of a user's head, covering only a portion of the scalp. This device also provides headphones attached to the head band. The head band of the Shimizu device is moveable between two or more positions relative to the user's scalp. In order to attain total scalp coverage that is needed for effective phototherapy treatment of hair loss, the head band of the Shimizu device must be moved to the several positions. This is due to the limited size and shape of the Shimizu head band, as well as variations in the shape of the human scalp. Accordingly, the Shimizu phototherapy device requires a minimum of two movements of the head band to cover the entire scalp, with a treatment performed at each position, thereby extending the overall time of an effective phototherapy treatment session that is needed for full scalp coverage.

Presently, there are clinical or salon based laser phototherapy devices (commercial devices) that are stationary and require a user to sit beneath them at a fixed location while undergoing treatment. These stationary commercial phototherapy systems are similar in nature to stationary hair dryers that are used at women's hair salons. More specifically, clinical or salon based laser therapy devices for hair growth include a hood that is positioned over a chair. These clinical or salon based stationary phototherapy systems are the only phototherapy systems known to provide simultaneous total scalp coverage without having to move or adjust the position of the head unit (i.e., hood) relative to the user's scalp. Laser hair therapy sessions for full scalp coverage treatments, using these clinical or salon based phototherapy laser systems, are typically about 20 minutes long. Thus, the Shimizu portable home phototherapy device, requiring a minimum of two movements of the headband, would extend the session to between 40 and 60 minutes for full scalp coverage. This extended phototherapy session time frame is beyond the norm for home use light-based therapies which should require no more than 15-25 minutes.

The present invention provides the home use equivalent of the clinical stationary laser phototherapy systems in a convenient and easy to use device that provides for simultaneous full scalp coverage. Moreover, the present invention provides the added benefit of ensuring a generally consistent distance from each of the light emitting sources to the scalp. This improves on the clinical or stationary laser phototherapy systems in which the distance between each of the light emitting sources and the scalp may vary from one person to the next due to the fact that they must adjust the hood or panel dependant on the height of the person being treated and/or the chair height. In clinical laser therapy systems, the distance between the lasers and the scalp may range between 2-5 inches. This is a significant limitation that the present invention overcomes. In particular, the intensity of the light source in low level laser therapies decreases significantly as the distance between the light emitting sources and the scalp increases. Further, because the human scalp is curved, use of a narrower headband, such as the one found on the Shimizu phototherapy device, will result in a variation of the distance between the light emitting sources and the scalp dependent upon the position of the headband relative to the scalp. For example, a curve of the head band necessary to contour to the rear or crown of the scalp would cause the head band to be at a greater distance from the treatment area when the head band is moved to the front of the scalp. This is due to the fact that the degree of curvature required for the crown of the scalp is not necessary for the front or temporal region of the scalp. Accordingly, while the fixed curvature of the head band may be ideally spaced relative to the scalp when positioned over the rear or crown of the scalp, when moved to the front or temporal region, the distance between the head band and the scalp would increase, thereby reducing the intensity of the light emitting sources and significantly decreasing the efficacy of the phototherapy treatment for the temporal region of the scalp.

The present invention seeks to address the limitations and shortcomings of the above described phototherapy treatment devices, by providing a canopy band having an array of light emitting sources optimally positioned relative to a human's scalp when the headband is properly worn on the user's head, and wherein the canopy band is specifically structured, shaped and disposed to provide simultaneous full scalp coverage. Moreover, the light emitting sources on the canopy band are positioned and arranged to provide complete and simultaneous light treatment coverage to the frontal, temporal and vertex (crown) regions of the scalp. Additionally, the present invention provides for spacing columns that extend downward from the inner side of the canopy band for comfortably and adjustably engaging the user's scalp, thereby maintaining the light emitting sources at a prescribed optimal distance from the user' scalp to ensure that the phototherapy treatment is consistent and of maximum efficacy.

A further embodiment of the invention provides for application of light from the array of light emitting sources to the face of the user. The phototherapy device is designed to maximize the efficiency of a variety of skin and scalp treatments, either singly or in combination, through use of either fixed or removable canopy bands or plates that are fitted with an array of light emitting sources.

SUMMARY OF THE INVENTION

The present invention is directed to a wearable hands-free apparatus that provides phototherapy to the scalp, skin tissue, and layers of a user's dermis. The phototherapy apparatus utilizes an array of light generating sources, which are housed within a unique canopy band or face plate that is structured and configured to provide complete and evenly distributed light to the entire scalp or face area being treated. For this application, the phrase "light generating sources" includes, but is not limited to, light emitting diodes (LEDs), laser diodes, infrared, and intense pulse lights (IPLs). The photobiostimulation process achieved by use of the phototherapy apparatus of this invention produces an increase in ATP and keratin production, enhancement in blood flow and circulation, as well as an increase in collagen production. As previously noted, phototherapy can be used to treat hair loss, and a number of skin and scalp conditions, such as acne, sunspots, wrinkle reduction, skin tightening, psoriasis, eczema and collagen production.

Each form of treatment requires light emitted within a particular wavelength range in order to be sufficiently absorbed into the skin tissue, to thereby treat a user's particular skin, scalp or hair-related condition. The canopy band or plate houses an array of light generating sources that are capable of emitting light within a range of output wavelengths in order to provide one or more penetration depths and photobiostimulation effects. In a further embodiment of the invention, each canopy band may contain an array of mixed light generating sources, wherein certain light generating sources emit light within one wavelength range, while other light generating sources emit light within different wavelength ranges, thereby targeting different areas of the cell.

In a preferred embodiment of the invention, the phototherapy apparatus is comprised of a head unit that includes the canopy band fitted with the array of light generating sources for treating hair and scalp related conditions. The canopy band is specifically designed to conform to the shape of the human scalp in order to provide complete light coverage to the scalp so that all areas that are most commonly affected by hair loss in both men and women can be simultaneously treated. The canopy band may be fixed as an integral part of the head unit or, alternatively, may be interchangeably attached by way of a releasable securing mechanism. Various embodiments of the releasable securing mechanism utilizing different methods of interchangeable attachment are contemplated.

According to the preferred embodiment of the present invention, the bottom or inner side of the canopy band, that is disposed in opposing relation to the user's scalp, is designed to follow the shape and curvature of the average adult human head and particularly the frontal, temporal and vertex regions of the scalp. These are the regions affected by hair loss. Specifically, the front portion of the canopy band is designed to follow the curvature and contour of the frontal and temporal regions of the scalp. Similarly, the rear portion of the canopy band is designed to extend slightly beyond the vertex (crown) of the head and is angled to cover the entire rear of the scalp affected by hair loss. The left and right sides of the canopy band are also configured to follow the curvature of the sides of the scalp. The light generating sources are positioned throughout the inner (bottom) side of the canopy band to provide complete light treatment coverage of the frontal, temporal and vertex regions of the scalp.

The head unit in the preferred embodiment further includes at least four spacing columns that extend from the inner side of the canopy for engaging the scalp and maintaining the inner side of the canopy, and particularly the light generating sources, at a fixed distance from the frontal, temporal and vertex regions of the scalp. The spacing columns screw into the inner side of the canopy band and are adjustable in length to allow the user to adjust the distance between the light generating sources and the scalp for comfort and proper light distribution onto the treated areas of the scalp. The distal ends of the spacing columns are fitted with rubber tips for engaging the scalp. The rubber tips are shaped for flexibility, comfort, weight displacement and conformity to variations in scalp contour. A ball joint connection allows the rubber tips to pivot relative to the distal ends of the spacing columns, thereby allowing for adjustable angular positioning of the tips to accommodate for variations in scalp shapes, sizes and contours of different users. Accordingly, the spacing columns serve to maintain the light generating sources at a prescribed optimal distance from the several regions of the scalp affected by hair loss, thereby ensuring that the phototherapy treatment is consistent and of maximum efficacy.

The light generating sources (e.g., diodes) may be adapted to pulse according to a proprietary algorithm that is programmed in the memory of a control device. In a preferred embodiment, the control device is a hand held unit that has an LCD display. Various hair loss treatments and/or skin therapy protocols for both men and women can be selected by pressing one of several buttons that correspond to the available treatments. The algorithm may provide for pulsed light in specific pre-determined patterns and timing sequences in accordance with the particular hair loss or skin related treatment that is selected.

BRIEF DESCRIPTION OF THE DRAWINGS

For a fuller understanding of the nature of the present invention, reference should be made to the following detailed description taken in conjunction with the accompanying drawings in which:

FIG. 9 is an exploded side elevational view of the embodiment of FIG. 7 showing the phototherapy apparatus of the present invention, in accordance with a preferred embodiment, as it is when dismantled into separate parts, and including a canopy band or plate with an array of light generating sources, a set of headphones, and a head support band;

FIG. 10 is an isolated view of the male component taken from FIG. 9, including two release buttons, and a releasing mechanism;

Like reference numerals refer to like referenced parts throughout the several views of the drawings.

DETAILED DESCRIPTION OF THE PREFERRED EMBODIMENTS

Referring to the several views of the drawings, the wearable hands-free apparatus that provides phototherapy treatment to the scalp, skin tissue, and layers of a user's dermis is shown according to several embodiments of the invention and is generally indicated as 10. The phototherapy apparatus 10 is specifically sized, structured and configured to be worn on a person's head.

Figure 3:
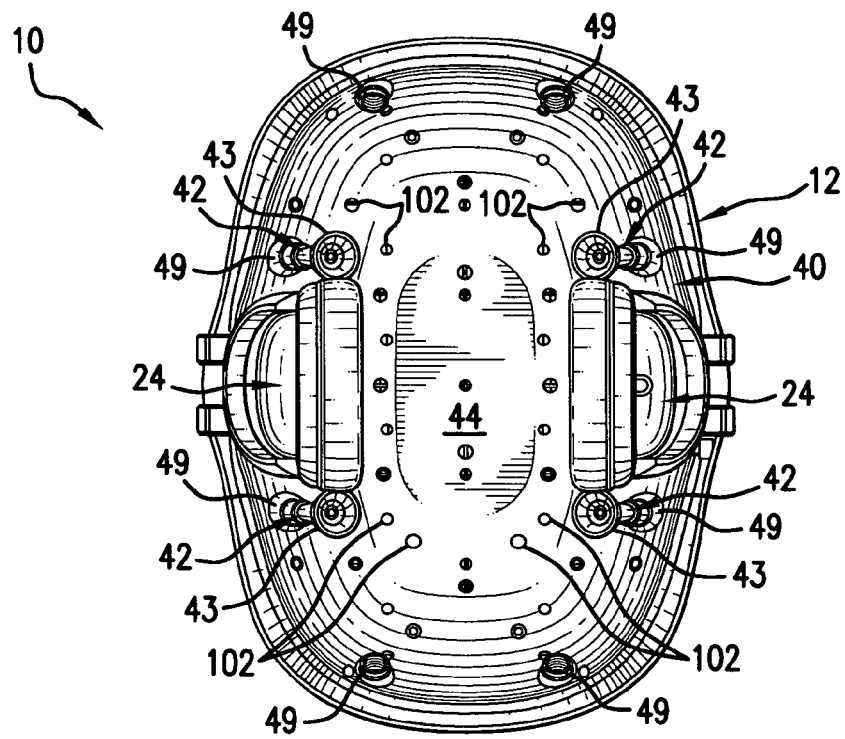
FIG. 3 is a bottom plan view of the head unit of the phototherapy apparatus of FIG. 1 showing the inner side of the canopy band, the arrangement of light generating sources, and the spacing columns at a normal position.

In each of the embodiments of the invention, the phototherapy apparatus 10 includes a head unit 12 (e.g., a headset, head phones, headband, or helmet) with left and right audio earphones 24 to allow the user to listen to an audio program during a phototherapy treatment. The head unit 12 supports a light emitting canopy band or plate 40 that houses an array of light generating sources 102 (see FIGS. 3-4 and 15), such as light emitting diodes (LEDs), lasers, infrared lights, or other suitable light sources that are adapted to emit light within a particular wavelength range correlating with the treatment of one or more specific hair loss, scalp and/or skin-related conditions.

Figure 1:
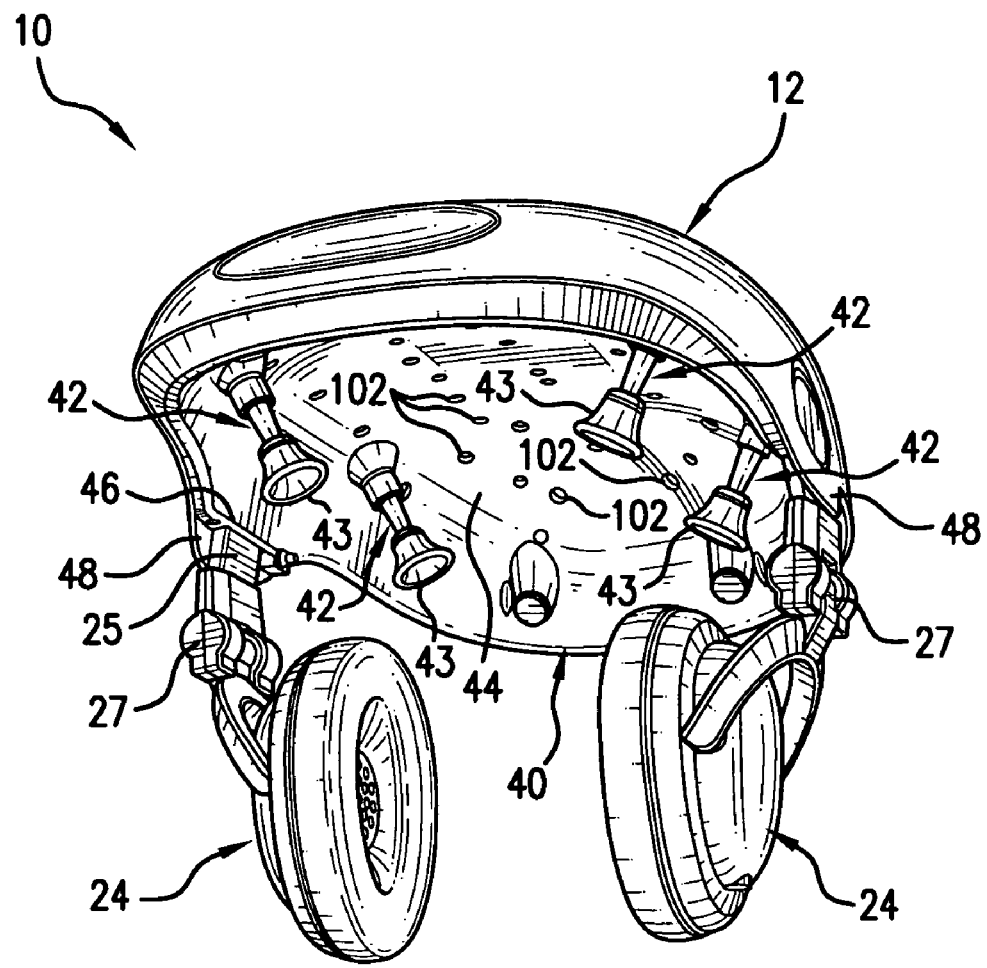
FIG. 1 is a front, bottom perspective view showing a head unit of a phototherapy apparatus in accordance with a preferred embodiment of the present invention, and wherein the head unit is sized, structured and configured to cover the scalp of a user and to generally conform to the curvature of the scalp, including the frontal, temporal, and vertex regions of the scalp, and wherein the head unit includes collapsible earphones and an array of light generating sources on an inner side of the canopy band for producing a light pattern that can be simultaneously directed onto the frontal, temporal and vertex regions of the user's scalp, and further wherein the canopy band includes at least four adjustably positionable spacing columns for engaging the user's head in order to maintain the light generating sources at a predetermined and uniform distance from the user's scalp.
Figure 2:
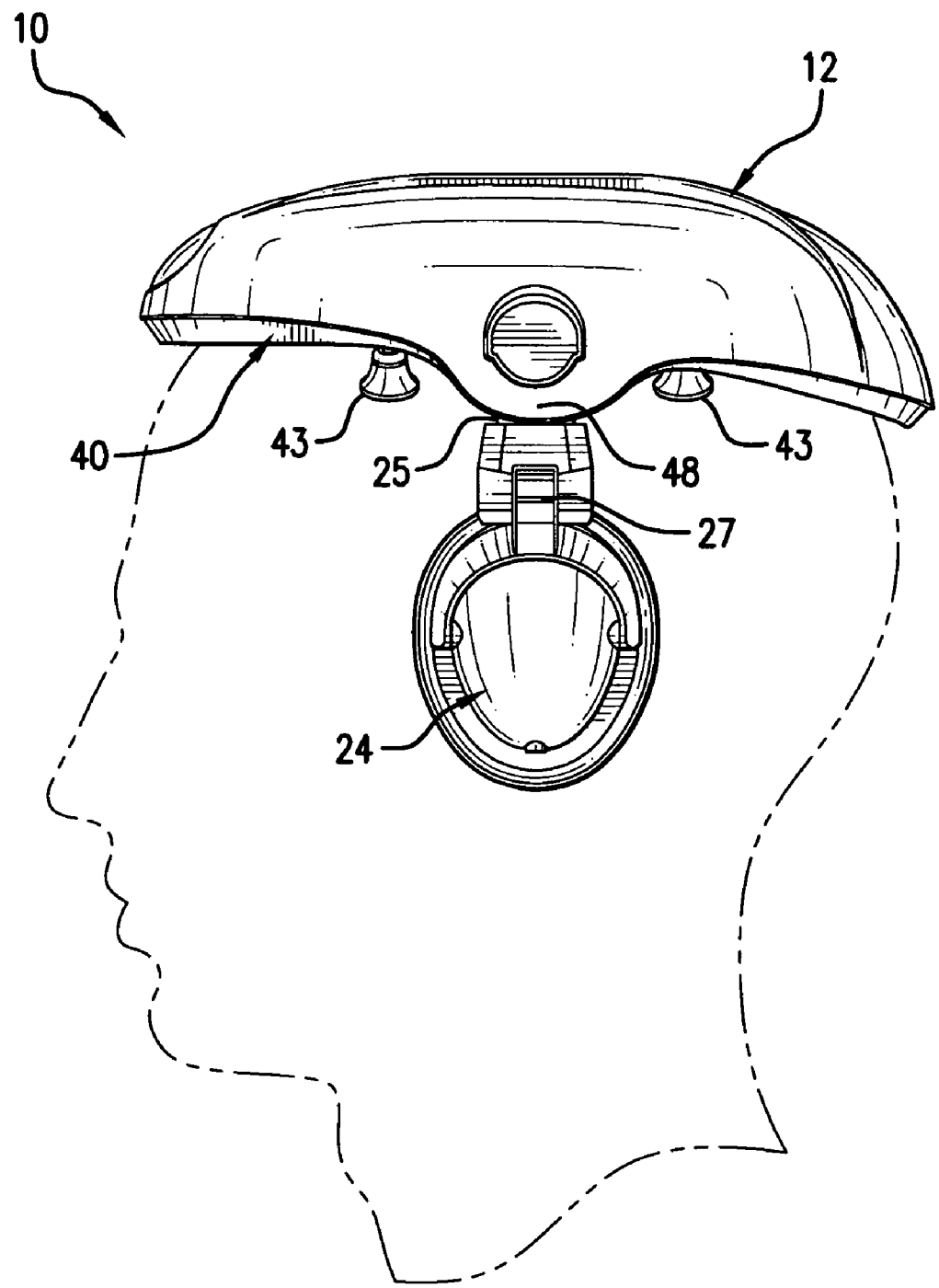
FIG. 2 is a side elevational view showing the head unit of the phototherapy apparatus of FIG. 1 being worn on a user's head.

A preferred embodiment of the phototherapy apparatus 10 is shown in FIGS. 1-6. In this preferred embodiment of the invention, the canopy band 40 is formed as an integral part of the head unit 12 and is specifically designed to conform to the shape of the human scalp for providing complete light coverage to the areas of the scalp that are most commonly affected by hair loss in both men and women. The canopy band 40, as seen in FIGS. 1 and 2, is slightly elongated at the front and rear ends to emphasize the unique shaping of the human scalp. The canopy band 40 is also designed with a slight taper from front to rear, to allow the light from the light generating sources 102 to be directed on the scalp to treat the frontal, temporal and vertex regions of the scalp, while covering the entire scalp for a complete phototherapy treatment. The underside surface 44 of the canopy band 40, disposed in spaced, opposing relation to the user's scalp (see FIG. 2), is fitted with the light emitting sources 102 (e.g., diodes) that may be adapted to pulse according to the proprietary algorithm that is programmed in the memory of a hand held control unit 110, shown in FIG. 20. This algorithm provides for pulsed light in specific predetermined patterns in order to treat a variety of hair loss conditions in both men and women.

Figure 4:
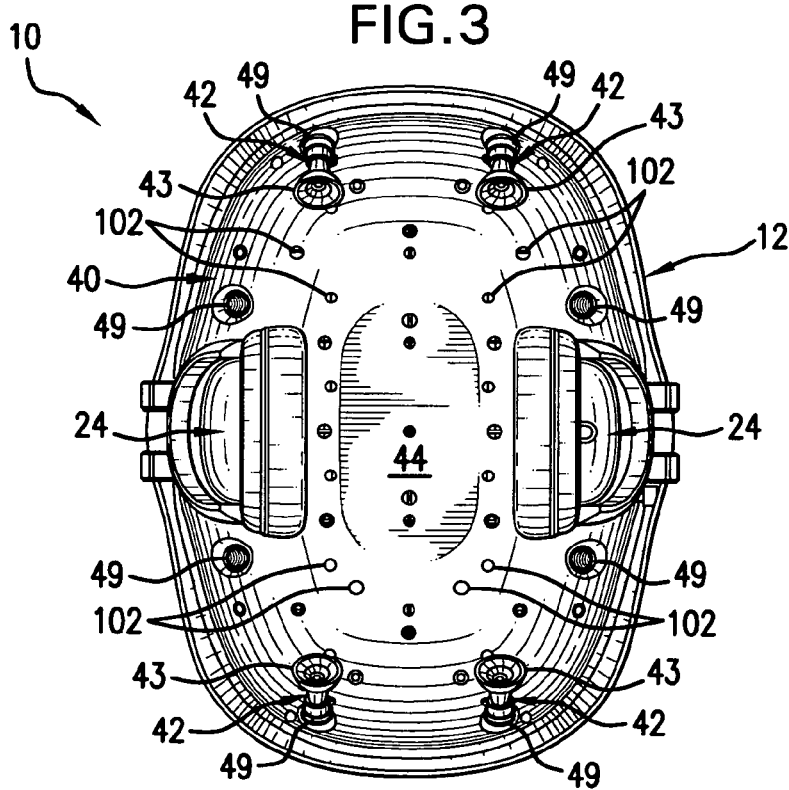
FIG. 4 is a bottom plan view of the head unit of the phototherapy apparatus of FIG. 1 showing the spacing columns moved to an adjusted position at the front and rear ends of the canopy band.
Figure 5:
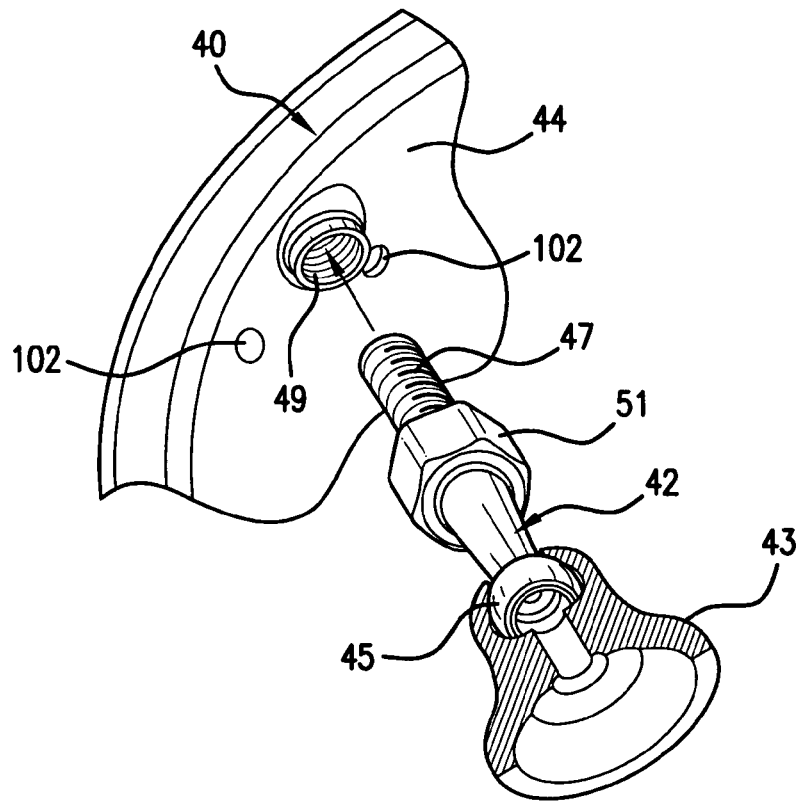
FIG. 5 is an isolated perspective view, in partial section, showing the structure of a spacing column including the manner of threaded attachment to the inner side of the canopy band and a ball pivot joint for allowing adjustable positioning of a bell-shaped tip that engages the user's head.

Forward and rear spacing columns 42 extend downwardly from the underside (i.e., inner side) 44 of the canopy band 40. Rubber bell-shaped tips 43 at the distal ends of the spacing columns 42 engage the user's head (e.g., the scalp) to maintain a predetermined space (i.e., gap) between the array of light generating sources 102 and the user's scalp, thereby ensuring proper light distribution and penetration of light into the cells in the scalp. The distal ends of the spacing columns 42 and rubber tips 43 are formed to provide a ball and socket arrangement, or ball joint 45, that allows for adjustable positioning of the rubber tips 43 relative to the spacing columns 42 in order to conform to the size, shape and surface contour of the user's head. The rubber tips 43 are shaped for flexibility, comfort, weight displacement and are adapted to conform to variations in scalp surface contour. The proximal ends 47 of the spacing columns 42 are threaded and screw into threaded ports 49 on the inner side 44 of the canopy band 40. This allows the spacing columns to be moved from the position shown in FIG. 3 to the extreme forward and rear position shown in FIG. 4. The ability to move the spacing columns to this position shown in FIG. 4 is useful in the event the user has had surgery or hair transplants to the temporal and/or vertex regions of the scalp. The screw thread attachment of the spacing columns 42 to the inner side 44 of the canopy band 40 also allows the user to adjust the length of each of the canopy bands, thereby allowing for controlled adjustment of the distance between the light generating sources 102 and the scalp for comfort and proper light distribution onto the treated areas of the scalp. A hexagonal hub 51 on the spacing columns allows for convenient grasping and threaded advancement for withdrawal of the spacing columns with the use of the fingertips.

Figure 6:
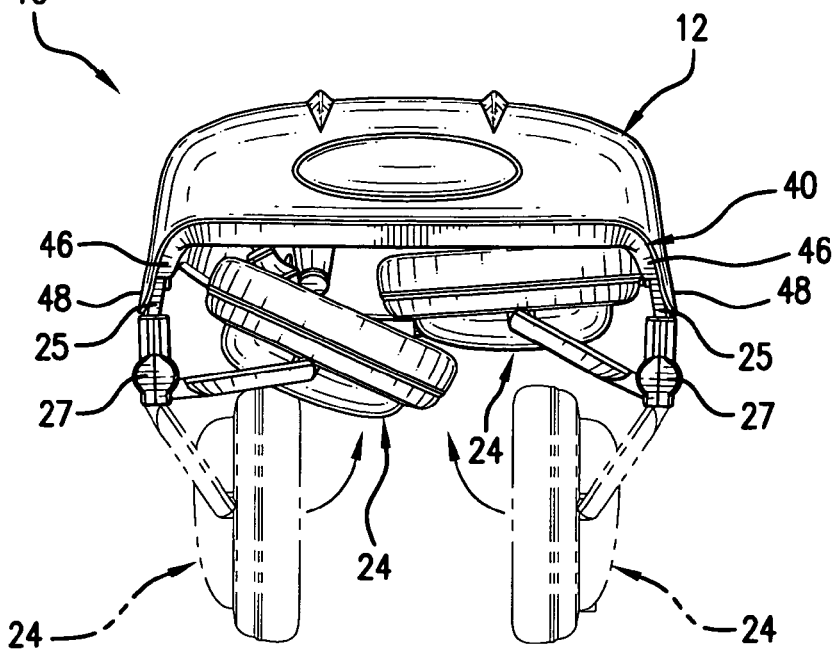
FIG. 6 is a front elevational view of the head unit of the phototherapy apparatus of FIG. 1 demonstrating movement of the earphones to a folded, collapsed position under the canopy band for storage and transport.

The left and right audio headphones 24 are adjustably supported on slidable arm members 25 that extend from the head unit 12 at the bottom ends 46 of downwardly extending portions 48 on the left and right sides of the head unit 12. The left and right audio headphones 24 are also adapted to fold inwardly and under the canopy band or plate 40, as shown in FIG. 6. Specifically, hinge members 27 connecting the headphones 24 to the arm members 25 allow the headphones to fold and collapse under the canopy band or plate 40 for convenient storage, packaging and transport.

Figure 20:
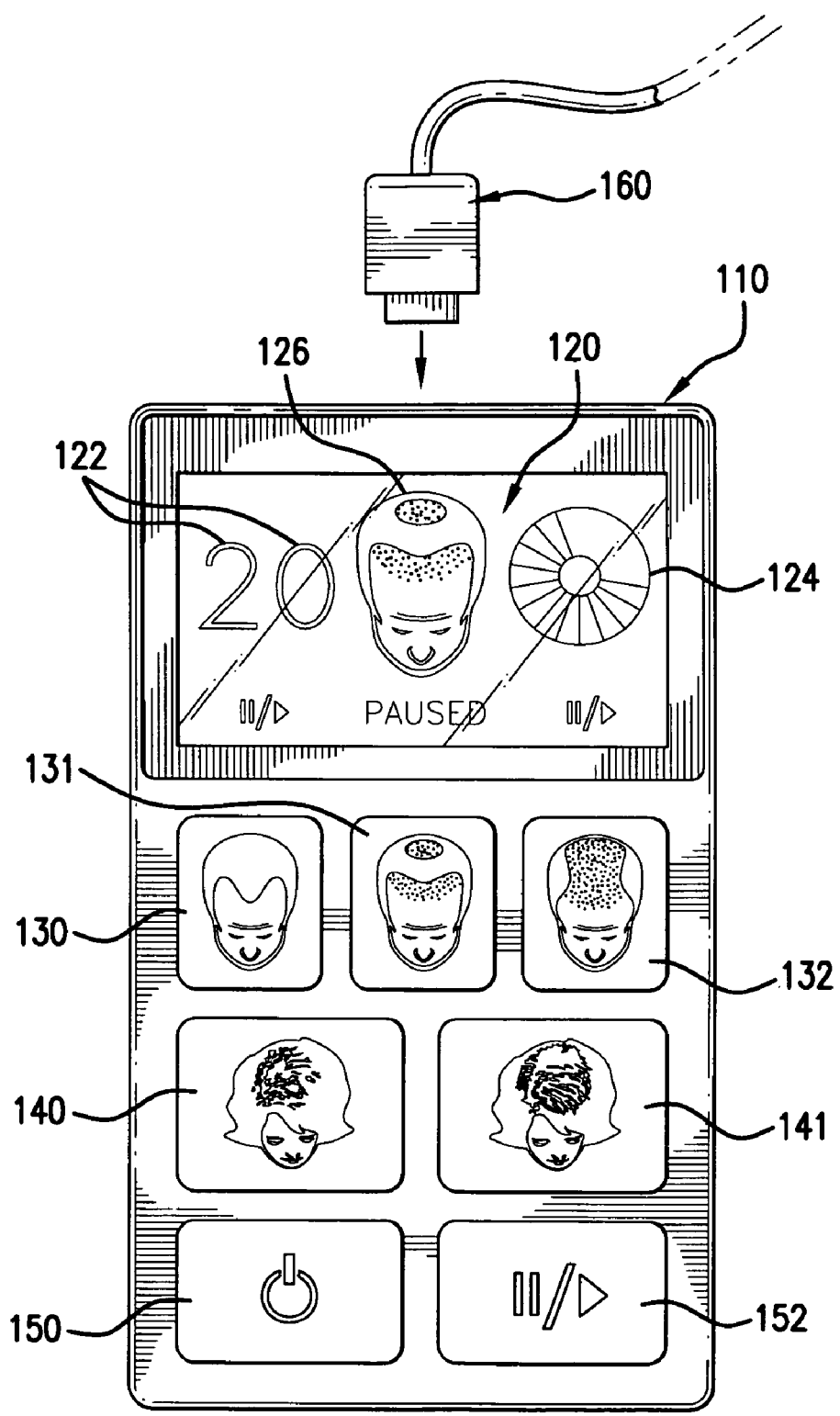
FIG. 20 is a top plan view of a hand held control unit that connects to the phototherapy apparatus for selecting timed phototherapy treatments according to the most common hair loss patterns or skin related conditions in both men and women, which specific illustrations of male and female baldness patterns shown on treatment selection buttons.

Referring to FIG. 20, the hand held control unit 110 is shown and includes an LCD display 120 with timer functions and treatment control and selection buttons. Specifically, the top LCD display 120 presents a two digit timer display 122 for indicating the number of minutes remaining in a particular phototherapy treatment. The opposite side of the top LCD display 120 presents a timer wheel 124 that counts down five second intervals of each minute. More specifically, the timer wheel includes an arrangement of spokes representing a certain number of seconds in the timer display function. During operation, a spoke on the timer wheel disappears after each five seconds of operation, within a one minute cycle. For example, during a twenty minute treatment, the two digit timer display 122 will present the number 20 and, at the beginning of the treatment the timer wheel will present twelve spokes. After every five seconds, one of the spokes on the timer wheel will disappear until the minute is up. Then, the number on the two digit display will change from 20 to 19 and the timer wheel will repopulate with 12 spokes to resume the countdown sequence for each minute of treatment. The illustration in the center of the top LCD display presents an image 126 of the top of a male or female head, with a particular balding pattern representing the specific treatment that has been selected. Below the top LCD display there is a row of three buttons 130, 131 and 132, each presenting an image of the top of a male scalp with illustrations of hair loss patterns that are common in men. The next row of treatment control buttons includes two female treatment controls 140, 141 with images of the top of a female scalp presenting two common hair loss patterns in women. The control unit 110 further includes an on/off button 150 and a start/pause button 152. When the user selects a particular hair loss treatment for either a man or woman, by pressing one of the five treatment buttons, the scalp image from the selected treatment is presented in the center of the top LCD display 120, indicating that this particular treatment has been selected. The user can then press the start button 152 which will start the timed automated phototherapy treatment session. The algorithm, programmed in the memory of the control unit, may provide for pulsed light from the diodes in the canopy band, in specific predetermined patterns in accordance with the particular hair loss treatment that is selected. The hand held control unit 110 connects to the head unit 12 by a wire 160 that extends from the hand held unit 110 and plugs into the head unit 12 at a designated port. The hand held unit stores all programmed functions of the phototherapy apparatus in memory including operational functions of the array of light generating sources 102, as well as all audio functions connected with the headphones 24 on the head unit 12. The hand held control unit 110 provides for selection of audio programs stored in memory, as well as volume and other audio functions.

Referring to FIG. 20, the various treatment selections on the handheld control unit 110 provide for various pulse durations of the light generating sources 102 (e.g., LED's) for a certain duration of time in order to treat the specific area of the scalp that is most affected by hair loss. Below are examples of pulse times of the array of LED's on the canopy band for treatment of various areas on the scalp. For each pulse of each LED, the LED goes on for a certain number of seconds and then off for one second and this pattern is then repeated throughout the treatment. All of the LED's are designed to pulse in the areas of the scalp that have the most hair loss according to the medical scale. The men's hair loss scale is known as the Hamilton-Norwood scale. The woman's hair loss scale is known as the Ludwig scale.

Examples of hair loss treatments and LED pulse patterns are as follows:

Men's Button 130: The front of the scalp and the back of the scalp (vertex) have minor thinning.

The pulse for these sections is as follows: Front 7 LED's and the back 10 LED's pulse at 2 seconds on and 1 second off. The surrounding LED's will pulse at 3 seconds on and 1 second off. The treatment time is 20 minutes.

Men's Button 131: The front of the scalp has moderate thinning and the middle of the scalp and the back of the scalp have minor thinning.

The pulse for these sections is as follows: Front 16 LED's pulse at 4 seconds on and 1 second off. The back 14 LED's pulse at 2 seconds on and 1 second off. The treatment time is 20 minutes.

Men's Button 132: The entire scalp has major thinning.

The pulse for these sections is as follows: All the 30 LED's throughout the entire array pulse at 4 seconds on and 1 second off. The treatment time is 25 minutes.

Women's Button 140: The entire scalp has minor to moderate thinning.

The pulse for these sections is as follows: The LED's located in the center from front to back pulse at 4 seconds on and 2 seconds off. The LED's that are located along the side of the scalp pulse for 2 seconds on and 1 second off. The treatment time is 20 minutes.

Women's Button 141: The entire scalp has moderate to major thinning.

The pulse for these sections is as follows: All the 30 LED's throughout the entire array pulse at 4 seconds on and 1 second off. The treatment time is 25 minutes.

The embodiment shown in FIGS. 7-11 provides for interchangeable canopy bands or plates. Each interchangeable canopy band 40 removably attaches to a supporting head unit that is meant to be worn on a user's head. In the embodiment shown in FIG. 7, the head unit is a headset unit 20. The canopy band 40 is supported by the headset unit such that light is directly emitted toward the user's face. The headset unit 20 includes a detachable, adjustable head support band 22, which can be adjusted for snuggly fitting on the user's head and is necessary to prevent the headphones from slipping. The headset unit 20 further includes two audio headphones 24 on opposite sides of the adjustable head support band 22, which are adapted to come in contact with the user's ears when the phototherapy apparatus 10 is properly worn on the user's head. An audio input 28 is located on the headset unit 20 and communicates with the two audio headphones 24, allowing the user to listen to an audio feed from any general audio device, such as an MP3 player (e.g., an iPod). An LCD timer and function display system 32 is located on the headset unit 20, which displays a countdown timer and user functions, such as output wavelength. An input for a rechargeable battery system 26 is also located on the headset unit 20.

Figure 8:
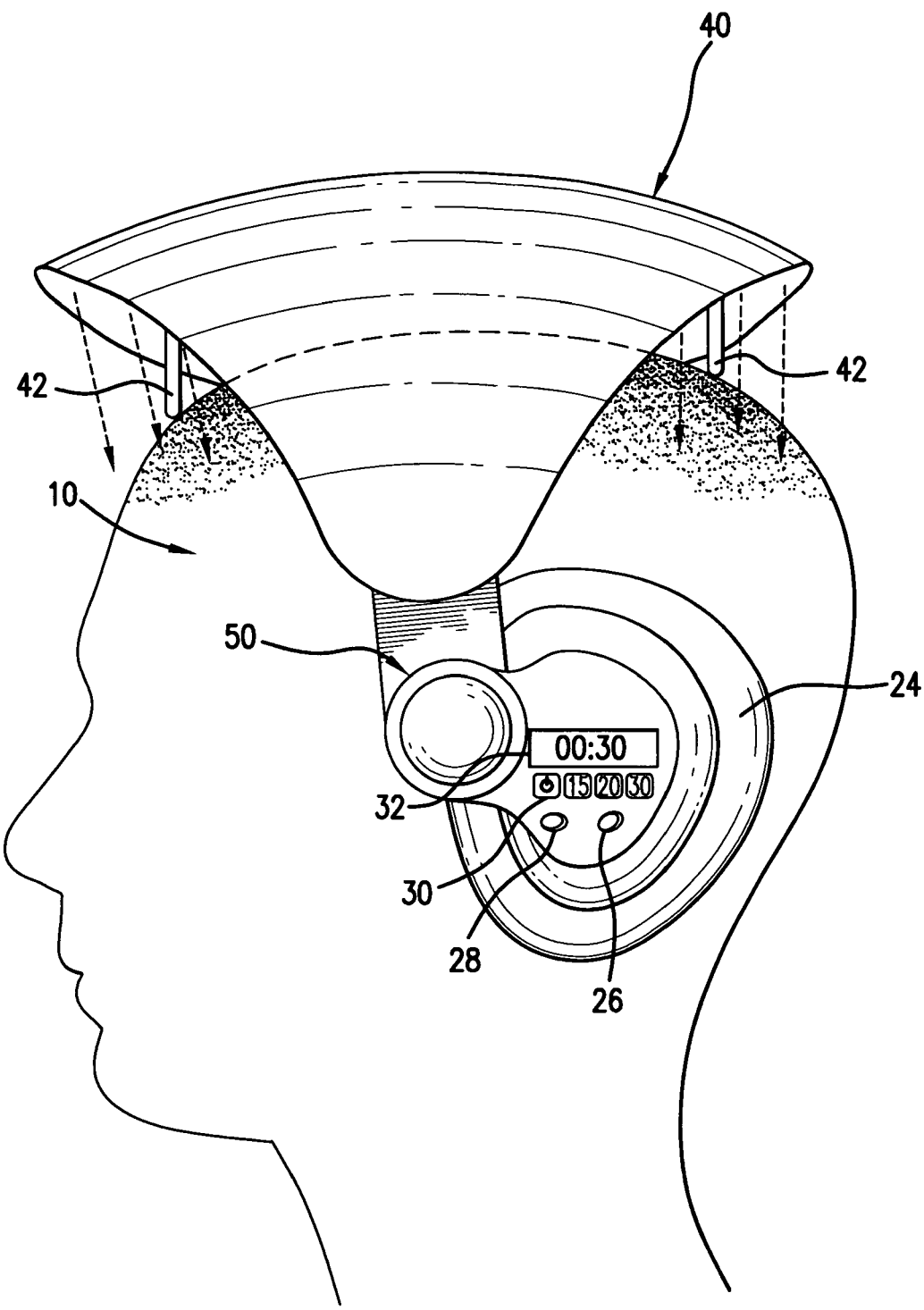
FIG. 8 is a side profile view showing the phototherapy apparatus of FIG. 7 and including a canopy band or plate with an array of light generating sources emitting light within a range of wavelengths, which is positioned in spaced, opposing relation to the user's scalp for treatment of hair and scalp conditions, canopy band spacing columns, a set of headphones, an interchangeable point for attaching or detaching canopy bands, a set of controls for controlling the operations of the apparatus, an LCD timer and function display system, an input for a rechargeable battery system, and an audio input.

FIG. 8 shows a further embodiment of the phototherapy apparatus 10 wherein the canopy band 40 is rotated such that light is directed toward the top of the user's head (scalp). This second embodiment is particularly intended for treatment of hair loss, scalp and hair wellness, which requires light emitted within a range (628 nm-694 nm) of red wavelengths, but can also be used to treat other skin-related conditions that are present on the user's scalp. Further illustrated in FIG. 8 is the inclusion of spacing columns 42 located on both the frontal and posterior portions of the canopy band 40, allowing for accurately maintained placement of the canopy band 40 relative to the user's head.

Figure 7:
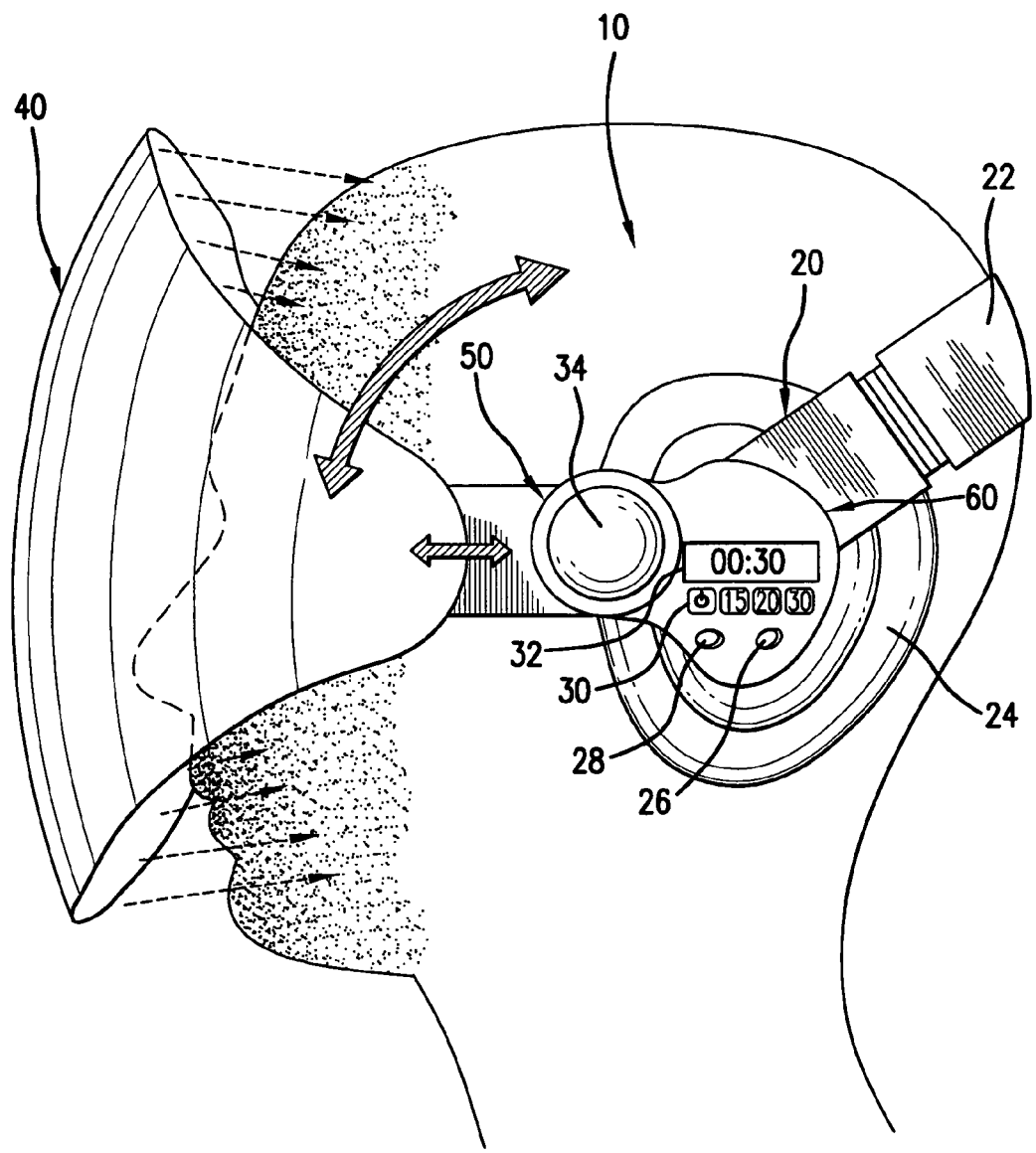
FIG. 7 is a side profile view showing the phototherapy apparatus of the present invention, in accordance with one embodiment, and including a canopy band or plate with an array of light generating sources emitting light within a range of wavelengths, which is positioned in spaced, opposing relation to the user's face, a headset unit, an interchangeable point for attaching or detaching canopy bands, a set of headphones, a set of controls for controlling the operations of the apparatus, an LCD timer and function display system, an input for a rechargeable battery system, and an audio input.

As illustrated in both FIGS. 7 and 8, there is a pivot mechanism 34 connected to the headphones 24, which allows for rotational movement of the canopy band 40 relative to the user's head, and consequently, complete scalp and facial coverage by the canopy band 40.

Figure 11:
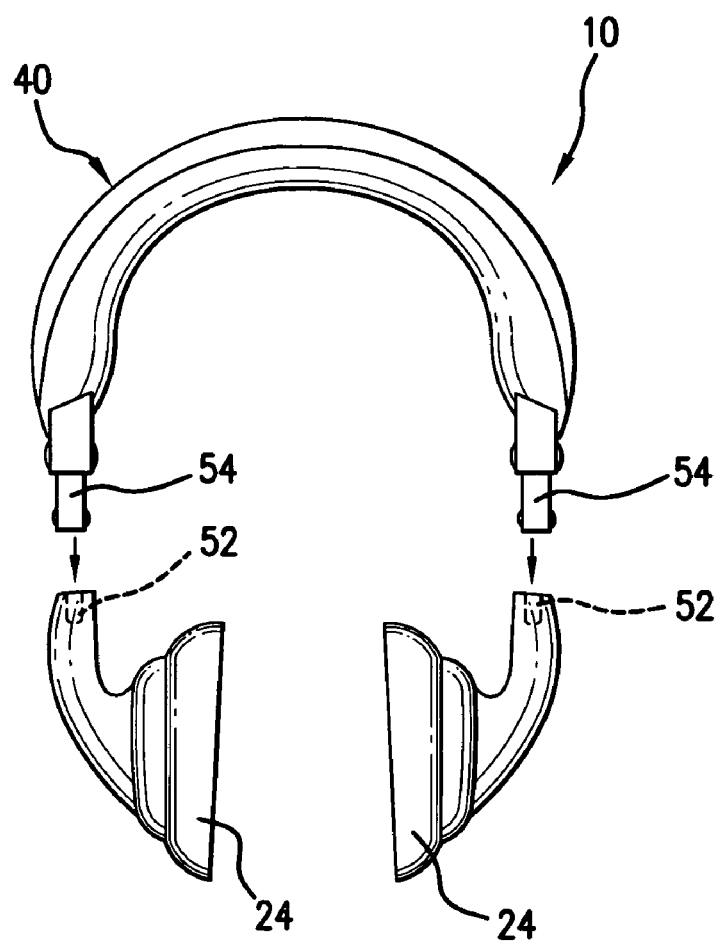
FIG. 11 is a front view showing the phototherapy apparatus of FIG. 7, as it is when dismantled into separate parts, and including a canopy band with an array of light generating sources and headphones.

As shown in FIGS. 9-11, on each side of the headset unit 20 is a female component 52 of a releasable securing mechanism 50. On opposite sides of each canopy band 40 is a male component 54 of the releasable securing mechanism 50. Each male component 54 has a release button 56 and a release mechanism 58. In operation, the male component 54 snaps into the female component 52 and securely fixes the canopy band 40 with the headset unit 20. In order to separate the canopy band 40 from the headset unit 20, the user must squeeze together the opposite ends of the release button 56, which will unhinge the release mechanism 58 and allow separation of the male component 54 from the female component 52.

Further illustrated in FIGS. 9 and 10 is the head support band securing mechanism 60, which helps support the phototherapy apparatus 10 upon the user's head when required. The head support band securing mechanism 60 is comprised of dual female components 62 that are located on the headphones 24, and duel male components 64 that are located on the head support band 22. In operation, the male component 64 snaps into the female component 62 and securely fixes the headphones 24 with the head support band 22. In order to separate the headphones 24 from the head support band 22, the user must squeeze together the opposite ends of the release button 66, which will unhinge the release mechanism 68 and allow separation of the male component 64 from the female component 62.

Figure 12:
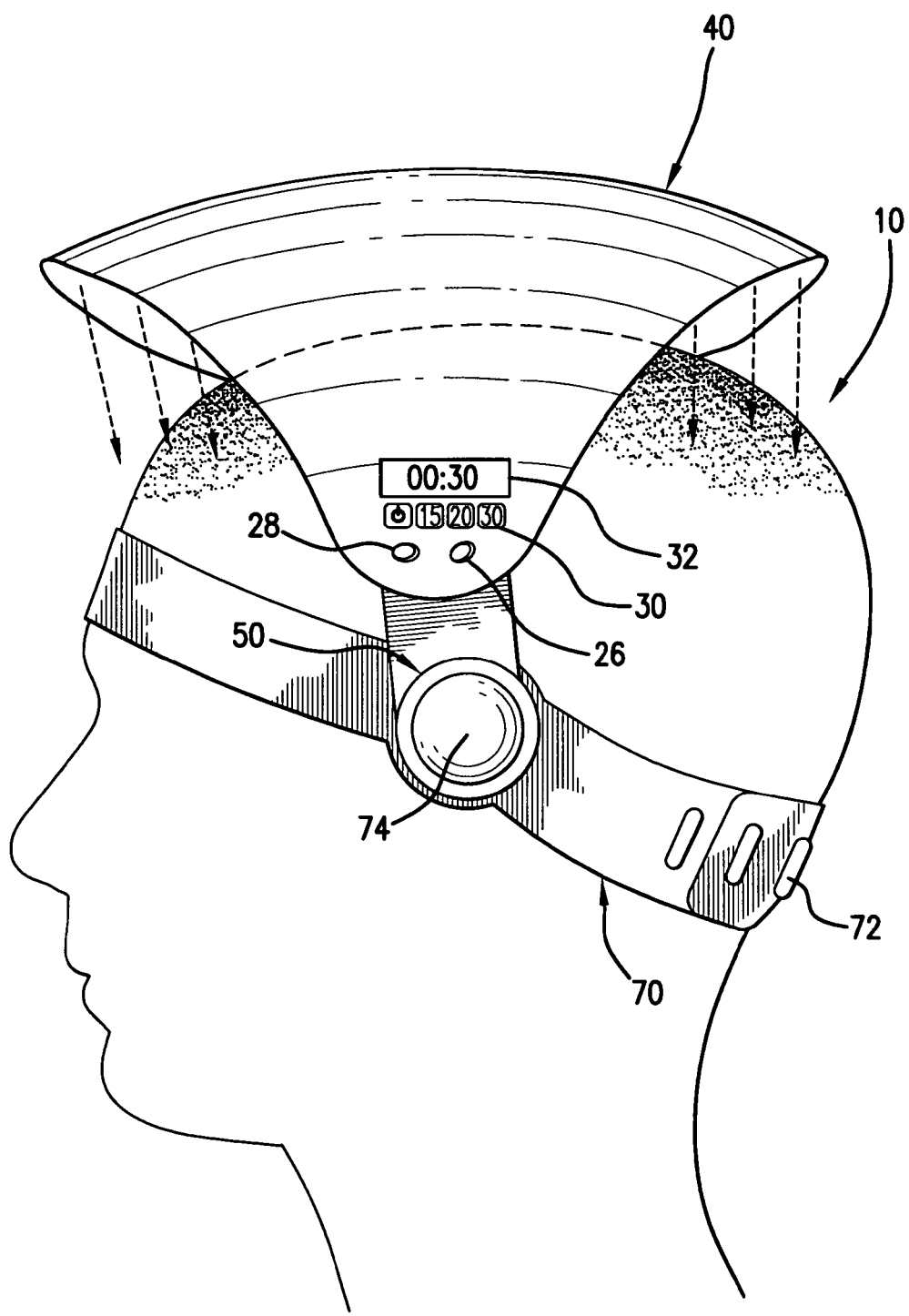
FIG. 12 is a side profile view showing the phototherapy apparatus of the present invention, in accordance with another embodiment, and including a canopy band or plate with an array of light generating sources, which is positioned in spaced, opposing relation to the user's scalp for treatment of hair and/or scalp conditions, an interchangeable point for attaching or detaching canopy bands, a headband unit, a headband securing mechanism, an LCD timer and function display system, an input for a rechargeable battery system, and an audio input.

In another embodiment of the phototherapy apparatus 10, as shown in FIG. 12, a canopy band 40 is supported by a headband unit 70, which is adapted to be worn on the user's head. The canopy band 40 houses an array of light generating sources 102 on its inner facing side 100 that provides evenly distributed phototherapy treatment to the user's scalp for treatment of hair-related conditions.

Figure 13:
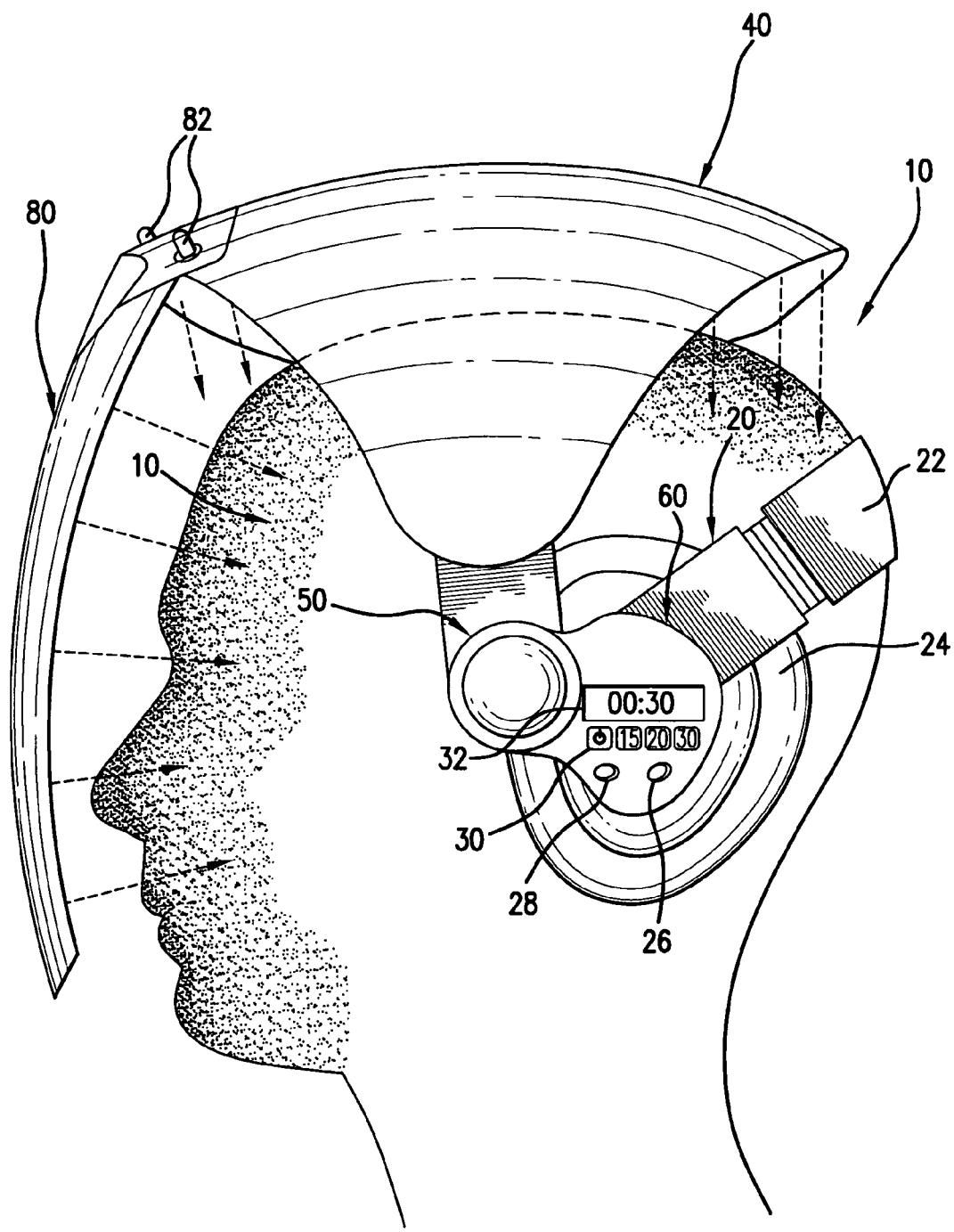
FIG. 13 is a side profile view showing the phototherapy apparatus of the present invention, in accordance yet a further embodiment, and including a fixed or detachable face plate with an array of light generating sources, which is positioned in spaced, opposing relation to the user's face, a canopy band with an array of light generating sources emitting light within a range of wavelengths, which is positioned in spaced, opposing relation to the user's scalp for treatment of hair-related conditions, a faceplate fastening mechanism, a headset unit, an interchangeable point for attaching or detaching canopy bands, a set of headphones, a set of controls for controlling the operations of the apparatus, an LCD timer and function display system, an input for a rechargeable battery system, and an audio input.

As illustrated in FIG. 13, the addition of a fixed or detachable face plate 80 connected to the canopy band 40 provides for a further embodiment of the phototherapy apparatus 10. The fixed or detachable face plate 80 houses an array of light generating sources 102 on its inner facing side, designed for providing evenly distributed phototherapy treatment to the user's face. This embodiment allows the user the option of treating both the scalp and face regions of the user's head, as the canopy band 40 in this embodiment is positionable in spaced, opposing relation to the scalp for treatment of hair-related conditions in the same manner as is provided in the second embodiment of the phototherapy apparatus 10.

As illustrated in both FIGS. 12 and 13, there is a headband proprietary pivot point 74 connected to the headband 70, which allows for rotational movement of the canopy band 40 relative to the user's head, and consequently, complete scalp and facial coverage by the canopy band 40.

Figure 14:
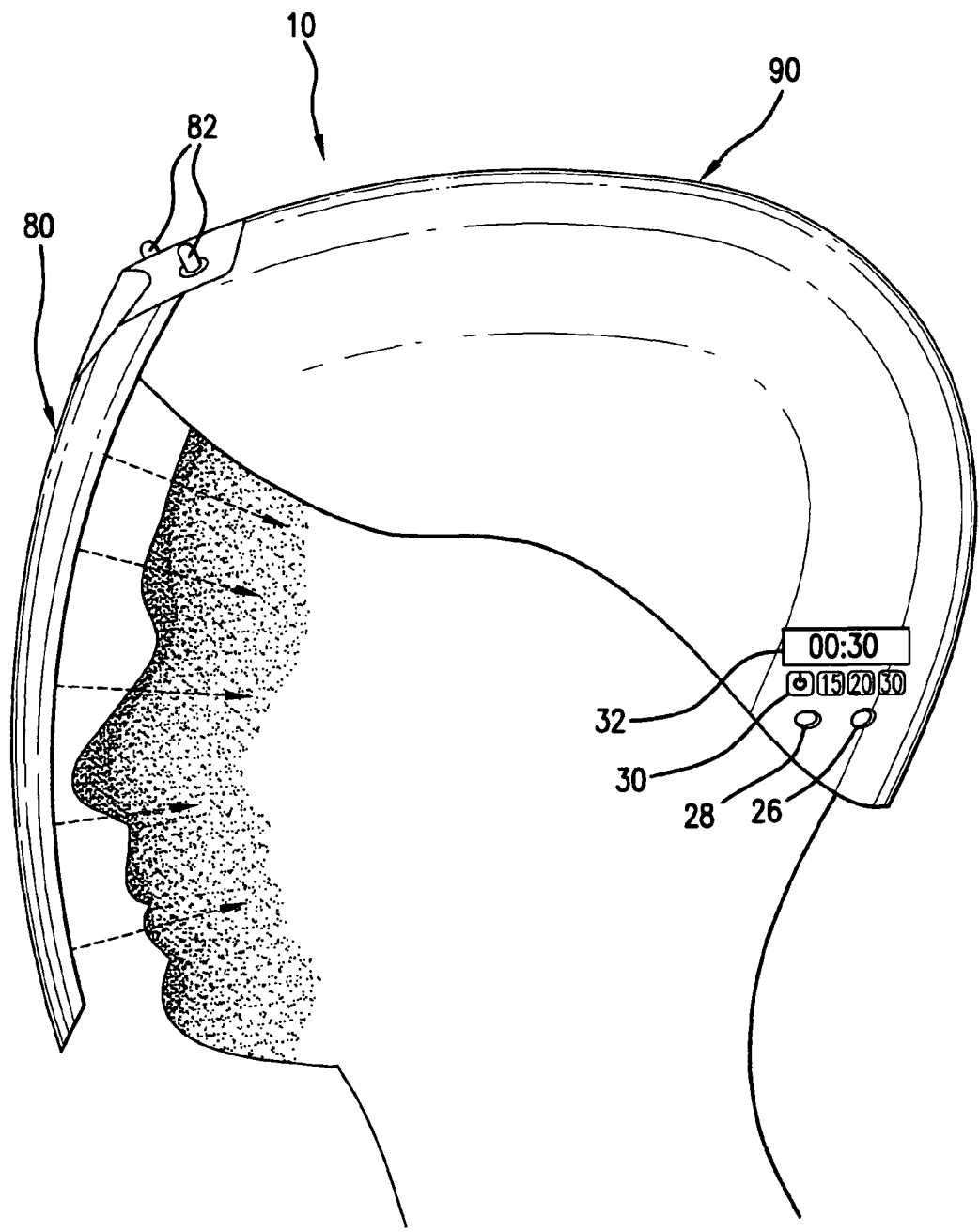
FIG. 14 is a side profile view showing the phototherapy apparatus of the present invention, in accordance with a further embodiment, and including a fixed or detachable face plate with an array of light generating sources, which is positioned in spaced, opposing relation to the user's face, a faceplate fastening mechanism, a helmet unit, a set of controls for controlling the operations of the apparatus, an LCD timer and function display system, an input for a rechargeable battery system, and an audio input.

Another embodiment of the phototherapy apparatus 10 is shown in FIG. 14, which illustrates a helmet unit 90 adapted to be worn on a user's head. Attached to the helmet unit 90 is a fixed or detachable face plate 80, which houses an array of light generating sources 102 on its inner facing side, designed for providing evenly distributed phototherapy treatment to the user's face.

Figure 15:
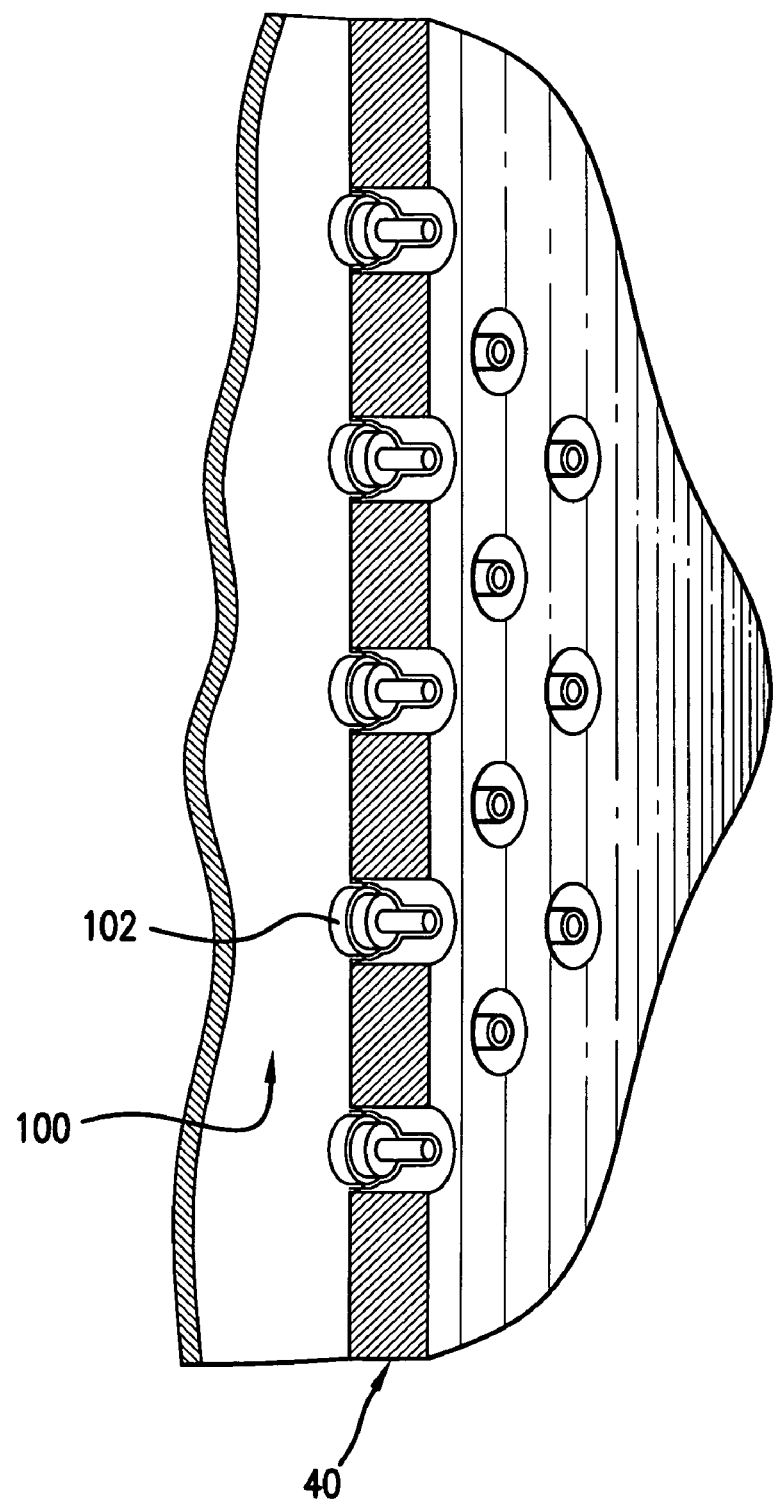
FIG. 15 is an isolated inner view of the canopy band or plate comprising an array of light generating sources mounted on the inner facing side of the canopy band or plate, showing the light consistency widening as it leaves the light generating source's aperture, as well as the resulting overlap of light on skin surface.
Figure 16:
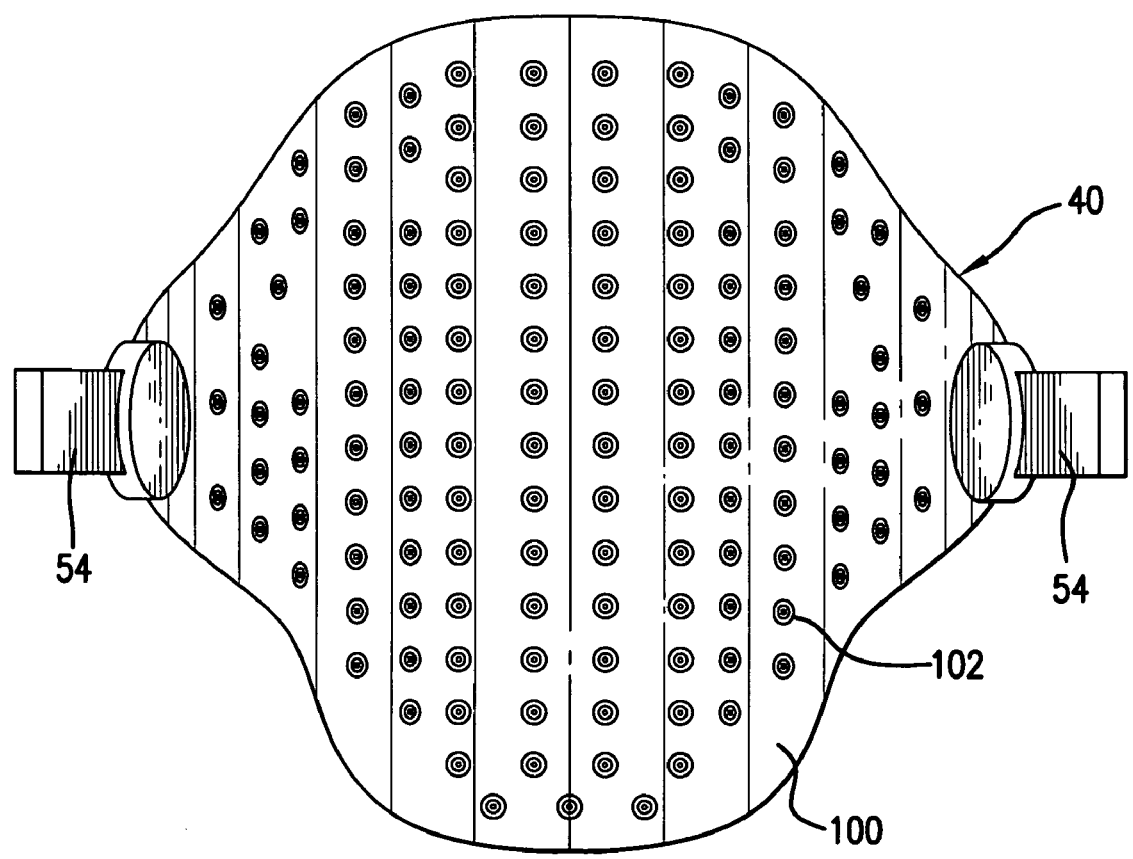
FIG. 16 is an isolated view of the inner facing side of a canopy band or plate, showing the array of light generating sources and the male component of the releasing mechanism.

As illustrated in FIGS. 15 and 16, an array of light generating sources 102 are mounted on the inner facing side 100 of a canopy band 40 that is positionable in spaced, opposing relation to a select area of the user's head. As an alternative to the array of light generating sources 102 being mounted on the inner facing side 100 of the canopy band 40, the array of light generating sources 102 can be snapped into place on the inner facing side 100 of the canopy band 40. In a further embodiment, the array of light generating sources 102 are composed of multiple wavelength light generating sources 102 within a single canopy band 40, wherein certain light generating sources 102 emit light within one particular wavelength range, while other light generating sources 102 emit light within different wavelength ranges. The spread of light from each light generating source 102 widens as it leaves the aperture, creating an overlap that provides a uniform distribution and intensity of light with enhanced penetration depth control to regions of skin tissue on the user's head. Additionally, protective eye wear can be worn by the user when the phototherapy apparatus 10 is being used to treat particular skin-related conditions on the face.

Figure 17:
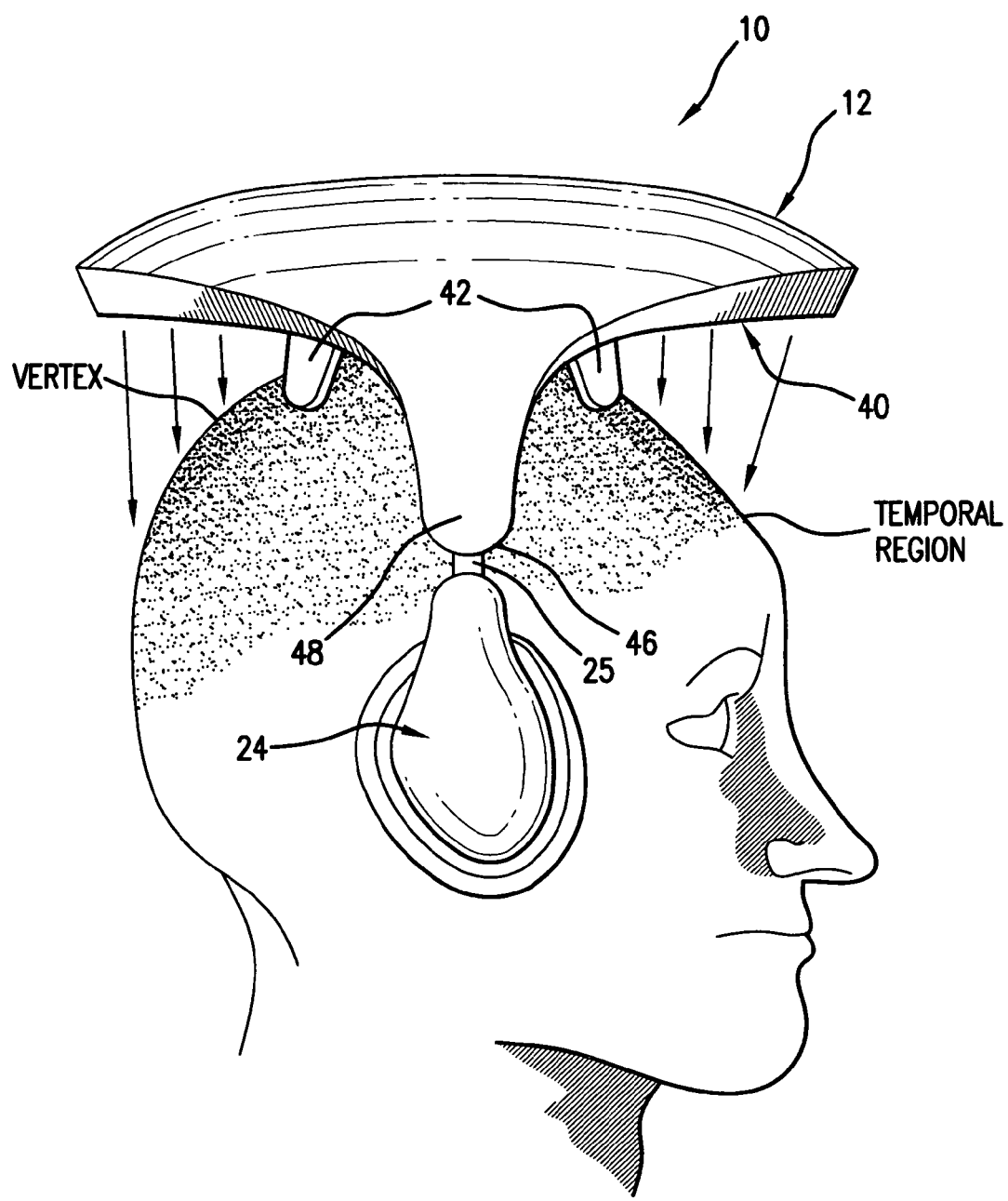
FIG. 17 is a side profile view showing the phototherapy apparatus of the present invention, in accordance with a preferred embodiment, and including a canopy band or plate fitted with an array light generating sources and earphones, and wherein the canopy band is specifically designed to conform to the shape of the human scalp for providing complete light coverage to the areas on the scalp that are most commonly affected by hair loss in both men and women.
Figure 18:
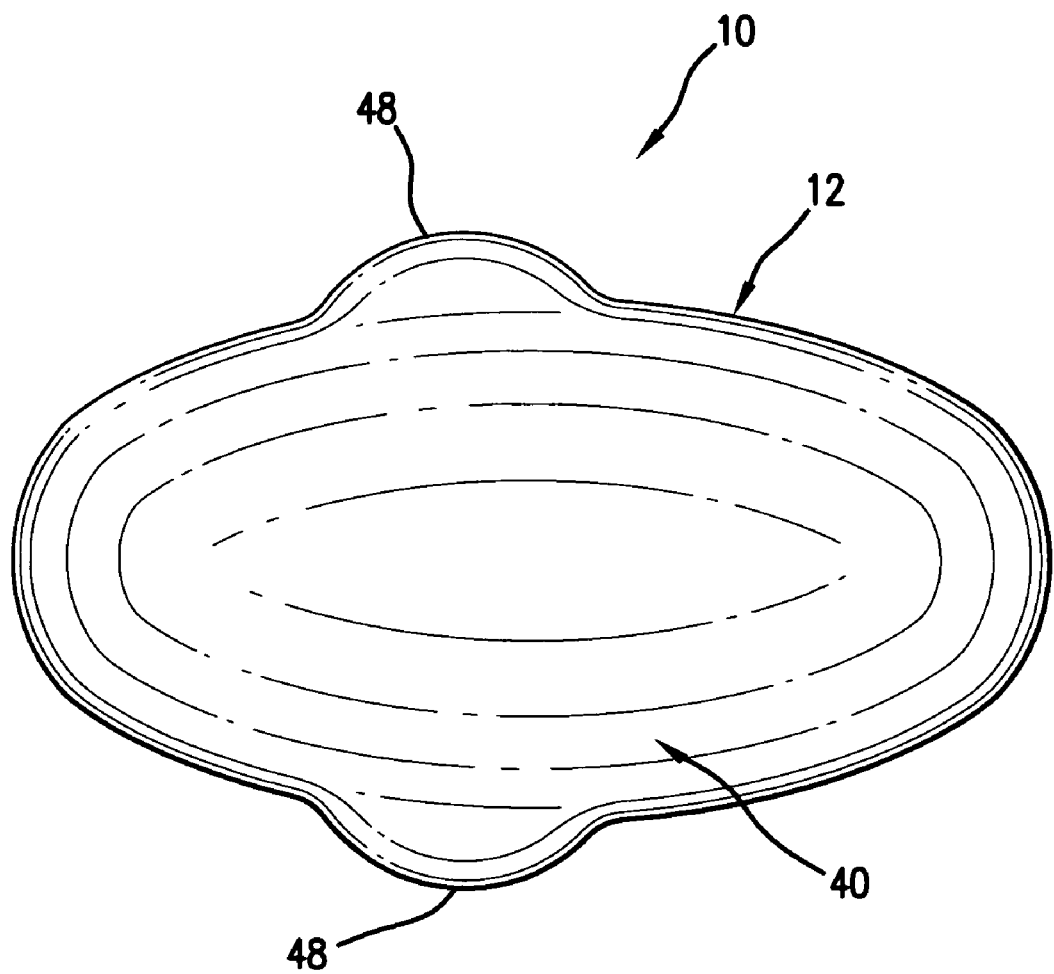
FIG. 18 is a top plan view of the canopy band of the embodiment of FIG. 17, illustrating the unique design that conforms to the shape of the human scalp to provide complete light coverage to the areas that are most commonly affected by hair loss in men and women.
Figure 19:
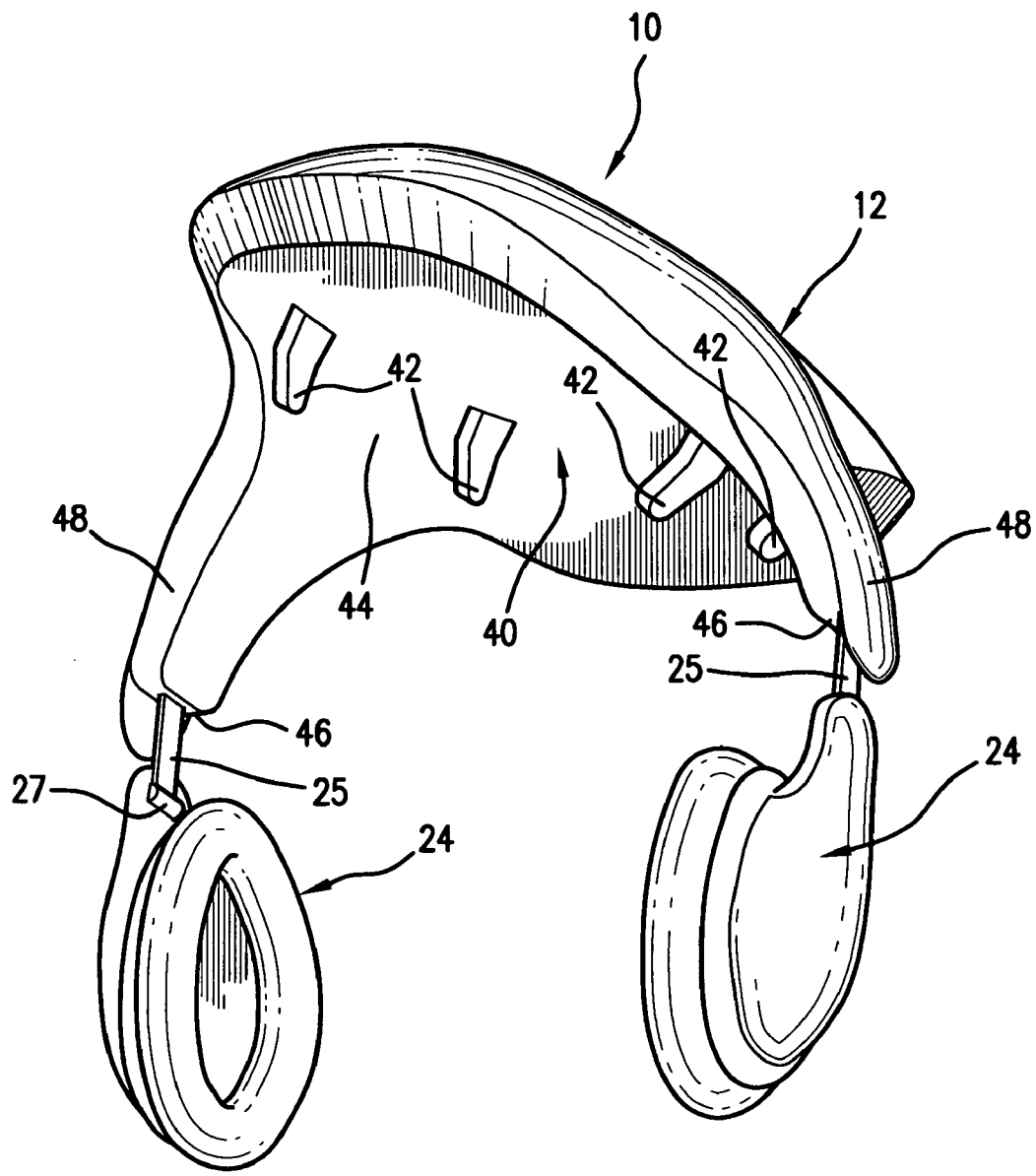
FIG. 19 is a perspective view of the phototherapy apparatus of FIG. 17.

FIGS. 17-19 illustrate yet a further embodiment of the phototherapy apparatus 10 which is similar to the preferred embodiment of FIGS. 1-6. In this embodiment (FIGS. 17-19) the canopy band 40 is formed as an integral part of the head unit 12 and is specifically designed to conform to the shape of the human scalp for providing complete light coverage to the areas of the scalp that are most commonly affected by hair loss in both men and women. As seen in FIG. 17, the canopy band 40 is slightly elongated at the front and rear ends to emphasize the unique shaping of the human scalp. The canopy band 40 is also designed with a slight taper from front to rear, to allow the light deposited on the scalp to treat the frontal, temporal and vertex regions of the scalp. Similar to the embodiment of FIGS. 1-6, this particular embodiment also provides for forward and rear spacing columns 42 that extend downwardly from the underside 44 of the canopy band or plate 40. Distal ends of the spacing columns 42 engage the user's head to maintain a predetermined distance between the array of light generating sources 102 and the user's scalp, thereby ensuring proper light distribution and penetration of light into the cells in the scalp. The left and right audio headphones 24 are adjustably supported on slidable arm members 25 that extend and retract into the head unit 12 at the bottom ends 46 of downwardly extending portions 48 on the left and right sides of the head unit 12. The left and right audio headphones 24 are also adapted to fold inwardly and under the canopy band 40, similar to the embodiment of FIGS. 1-6. The hinge members 27 connecting the headphones 24 to the arm members 25 allow the headphones to fold and collapse under the canopy band 40 for convenient storage, packaging and transport.

In each of the embodiments shown, depending on the type of condition being treated, light emitted at a particular output wavelength range is required to sufficiently penetrate the skin tissue. For example, in treating inflammation, lesions, or canker sores, a range (628 nm-694 nm) of red wavelengths is preferable; in treating rosacea or wrinkling of the skin, a range (568 nm-590 nm) of yellow wavelengths is preferable; in treating acne, a range (405 nm-476 nm) of blue wavelengths is preferable; in treating age spots, sun damage, or hyperpigmentation, a range (514 nm-543 nm) of green wavelengths is preferable; and in stimulating the skin to produce collagen and elastin, a range (700-1090 nm) of infrared wavelengths is preferable. For treating hair loss, light generating sources with a 670 nm output wavelength will produce a penetration depth of approximately 2-8 mm for direct treatment of hair cells.

It is noted that in each of the embodiments of the phototherapy apparatus 10 shown and described above, electric power for energizing the array of light generating sources may be supplied by disposable or rechargeable batteries carried in the head unit 12 or hand held control device 110. Alternatively, the head unit may plug into a standard wall outlet (e.g., a 110 volt outlet) for supplying electric power to the light generating sources. Similarly, electric power for energizing the audio source and functions, as well as the LCD display 120 and control circuitry of the hand held device 110 can be supplied by disposable or rechargeable battery power or by plugging into a standard wall outlet.

While the invention has been shown and described in accordance with several preferred and practical embodiments thereof, it is recognized that departures from the instant disclosure of the invention are fully contemplated within the spirit and scope of the invention and such changes, variations and modifications of the present invention are not to be limited except as recited in the following claims as interpreted under the Doctrine of Equivalents.

What is claimed is:

1. A wearable hands-free apparatus for providing phototherapy treatment to a user, said apparatus comprising:
    a head unit adapted to be worn on the user's head and including a pair of audio emitting earphones positionable on the user's ears and at least one canopy band;
    said at least one canopy band including an inner side that is positionable in spaced, opposing relation to the scalp of the user's head when the head unit is worn on the user's head, and said inner side being structured and configured to follow the curvature of the scalp, including the frontal, temporal and vertex regions of the scalp;
    an array of light generating sources on said inner side of said at least one canopy band and said array of light generating sources being positioned, structured and disposed for producing a light pattern that can be simultaneously directed onto the frontal, temporal and vertex regions of the user's scalp, and each of said light generating sources being further structured and disposed for emitting light within a wavelength range according to a particular condition being treated by phototherapy using the apparatus;
    a plurality of spacing columns structured and disposed to extend downwardly from the inner side of the canopy band, and each of the plurality of spacing columns including a distal end and a resilient tip pivotally fitted on the distal end for engaging the user's head, and the plurality of spacing columns maintaining the inner side of the canopy band in spaced relation to the user's scalp, and the resilient tip on the distal end of each of the plurality of spacing columns being adjustably positionable relative to the spacing column in order to conform to the user's head shape and comfortably engage the user's head; and
    at least one control for controlling operation of each of the light generating sources in said array of light generating sources.

2. The apparatus as recited in claim 1 wherein said light generating sources are light emitting diodes (LEDs).

3. The apparatus as recited in claim 1 wherein said light generating sources are laser diodes.

4. The apparatus as recited in claim 1 wherein said light generating sources are intense pulse lights (IPLs).

5. The apparatus as recited in claim 1 wherein said light generating sources are infrared lights.

6. The apparatus as recited in claim 1 wherein said at least one control is a hand held device with an LCD display, and said hand held device including a programmable memory for storing an algorithm that controls the timing and pulse rate of said array of light generating sources in accordance with a plurality of specific phototherapy treatments.

7. The apparatus as recited in claim 1 wherein said inner side of said at least one canopy band further includes a plurality of threaded ports.

8. The apparatus as recited in claim 7 wherein each of the plurality of spacing columns further includes a proximal end and a threaded head for selectively screwing into said plurality of threaded ports.

9. The apparatus as recited in claim 1 wherein said inner side of said at least one canopy band further includes a plurality of threaded ports.

10. The apparatus as recited in claim 9 wherein each of the plurality of spacing columns further includes a proximal end and a threaded head for selectively screwing into said plurality of threaded ports.

11. A wearable hands-free phototherapy apparatus for treatment of a user's scalp and for promoting hair growth, said apparatus comprising:
    a head unit adapted to be worn on the user's head;
    at least one canopy band on said head unit and including an inner side that is positionable in spaced, opposing relation to a user's scalp when the head unit is worn on the user's head;
    an array of light generating sources on said inner side of said at least one canopy band and being structured and disposed for producing a light pattern that can be simultaneously directed onto the frontal, temporal and vertex regions of the user's scalp, and each of said light generating sources being further structured and disposed for emitting light within a selected wavelength range according to a particular condition being treated by phototherapy;
    a plurality of spacing columns structured and disposed to extend downwardly from the inner side of the canopy band, and each of the plurality of spacing columns including a distal end and a resilient tip pivotally fitted on the distal end for engaging the user's head, and the plurality of spacing columns maintaining the inner side of the canopy band in spaced relation to the user's scalp, and the resilient tip on the distal end of each of the plurality of spacing columns being adjustably positionable relative to the spacing column in order to conform to the user's head shape and comfortably engage the user's head; and
    at least one control on said apparatus for controlling operation of said array of light generating sources.

12. The apparatus as recited in claim 11 wherein said light generating sources are light emitting diodes (LEDs).

13. The apparatus as recited in claim 11 wherein said light generating sources are laser diodes.

14. The apparatus as recited in claim 11 wherein said light generating sources are intense pulsed lights (IPLs).

15. The apparatus as recited in claim 11 wherein said light generating sources are infrared lights.

16. A wearable hands-free apparatus for providing phototherapy treatment to a user, said apparatus comprising:
    a head unit adapted to be worn on the user's head and including a pair of audio emitting earphones positionable on the user's ears and at least one canopy band;

said at least one canopy band including an inner side that is positionable in spaced, opposing relation to the scalp of the user's head when the head unit is worn on the user's head, and said inner side being structured and configured to follow the curvature of the scalp, including the frontal, temporal and vertex regions of the scalp, and said at least one canopy band being elongated at the front and rear ends and tapered from front to rear;

an array of light generating sources on said inner side of said at least one canopy band and said array of light generating sources being positioned, structured and disposed for producing a light pattern that can be simultaneously directed onto the frontal, temporal and vertex regions of the user's scalp, and each of said light generating sources being further structured and disposed for emitting light within a wavelength range according to a particular condition being treated by phototherapy using the apparatus;

a plurality of threaded ports on said inner side of said at least one canopy band;

a plurality of spacing columns structured and disposed to extend downwardly from the inner side of the canopy band, and each of the plurality of spacing columns including a distal end and a resilient tip pivotally fitted on the distal end for engaging the user's head, and the plurality of spacing columns maintaining the inner side of the canopy band in spaced relation to the user's scalp, and the resilient tip on the distal end of each of the plurality of spacing columns being adjustably positionable relative to the spacing column in order to conform to the user's head shape and comfortably engage the user's head, and each of the plurality of spacing columns including a proximal end and a threaded head for selectively screwing into said plurality of threaded ports to allow adjustable positioning of the spacing columns relative to the user's head; and at least one control for controlling operation of each of the light generating sources in said array of light generating sources.

17. The apparatus as recited in claim 16 wherein said light generating sources are light emitting diodes (LEDs).

18. The apparatus as recited in claim 16 wherein said light generating sources are laser diodes.

19. The apparatus as recited in claim 16 wherein said light generating sources are intense pulse lights (IPLs).

20. The apparatus as recited in claim 16 wherein said light generating sources are infrared lights.

21. The apparatus as recited in claim 16 wherein said at least one control is a hand held device with an LCD display, and said hand held device including a programmable memory for storing an algorithm that controls the timing and pulse rate of said array of light generating sources in accordance with a plurality of specific phototherapy treatments.

* * * * *